(12) United States Patent
Li et al.

(10) Patent No.: US 11,779,548 B2
(45) Date of Patent: Oct. 10, 2023

(54) ARYLFLUOROSULFATE COMPOUNDS AND METHODS

(71) Applicant: THE SCRIPPS RESEARCH INSTITUTE, La Jolla, CA (US)

(72) Inventors: Jie Li, San Diego, CA (US); Zilei Liu, San Diego, CA (US); Suhua Li, Guangzhou (CN); Peng Wu, San Diego, CA (US); K. Barry Sharpless, La Jolla, CA (US)

(73) Assignee: THE SCRIPPS RESEARCH INSTITUTE, La Jolla, CA (US)

( * ) Notice: Subject to any disclaimer, the term of this patent is extended or adjusted under 35 U.S.C. 154(b) by 687 days.

(21) Appl. No.: 16/871,902

(22) Filed: May 11, 2020

(65) Prior Publication Data
US 2020/0268683 A1    Aug. 27, 2020

Related U.S. Application Data

(60) Continuation of application No. 16/243,761, filed on Jan. 9, 2019, now abandoned, which is a
(Continued)

(51) Int. Cl.
| | | |
|---|---|---|
| A61K 31/05 | (2006.01) | |
| A61K 31/136 | (2006.01) | |
| C07C 305/26 | (2006.01) | |
| C07K 1/113 | (2006.01) | |
| C07K 1/02 | (2006.01) | |
| A61K 51/04 | (2006.01) | |
| A61K 38/31 | (2006.01) | |
| A61K 31/7048 | (2006.01) | |
| A61K 31/70 | (2006.01) | |
| A61K 31/655 | (2006.01) | |
| A61K 31/65 | (2006.01) | |
| A61K 31/56 | (2006.01) | |
| A61K 31/5513 | (2006.01) | |
| A61K 31/53 | (2006.01) | |
| A61K 31/515 | (2006.01) | |
| A61K 31/505 | (2006.01) | |
| A61K 31/485 | (2006.01) | |
| A61K 31/4745 | (2006.01) | |
| A61K 31/473 | (2006.01) | |
| A61K 31/4709 | (2006.01) | |
| A61K 31/47 | (2006.01) | |
| A61K 31/439 | (2006.01) | |
| A61K 31/4353 | (2006.01) | |

(Continued)

(52) U.S. Cl.
CPC ............ *A61K 31/05* (2013.01); *A61K 31/136* (2013.01); *A61K 31/14* (2013.01); *A61K 31/197* (2013.01); *A61K 31/198* (2013.01); *A61K 31/397* (2013.01); *A61K 31/40* (2013.01); *A61K 31/407* (2013.01); *A61K 31/4045* (2013.01); *A61K 31/4168* (2013.01); *A61K 31/4245* (2013.01); *A61K 31/439* (2013.01); *A61K 31/4353* (2013.01); *A61K 31/47* (2013.01); *A61K 31/473* (2013.01); *A61K 31/4709* (2013.01); *A61K 31/4745* (2013.01); *A61K 31/485* (2013.01); *A61K 31/505* (2013.01); *A61K 31/515* (2013.01); *A61K 31/53* (2013.01); *A61K 31/5513* (2013.01); *A61K 31/56* (2013.01); *A61K 31/65* (2013.01); *A61K 31/655* (2013.01); *A61K 31/70* (2013.01); *A61K 31/7048* (2013.01); *A61K 38/31* (2013.01); *A61K 47/54* (2017.08); *A61K 51/0497* (2013.01); *C07C 305/26* (2013.01); *C07D 277/82* (2013.01); *C07D 295/088* (2013.01); *C07D 295/185* (2013.01); *C07D 295/26* (2013.01); *C07K 1/02* (2013.01); *C07K 1/1136* (2013.01); *C07K 2/00* (2013.01); *C40B 30/06* (2013.01); *C07C 2601/14* (2017.05); *C07C 2603/18* (2017.05); *C12N 5/0693* (2013.01); *C12N 2503/02* (2013.01); *C40B 30/04* (2013.01); *C40B 40/04* (2013.01); *C40B 50/08* (2013.01); *G01N 2500/00* (2013.01)

(58) Field of Classification Search
CPC ...... A61K 31/05; C07D 295/26; C40B 30/06; C40B 30/04; C40B 40/04; C12N 5/0693; C12N 2503/02
See application file for complete search history.

(56) References Cited

PUBLICATIONS

Liu, Zilei, et al. "SuFEx click chemistry enabled late-stage drug functionalization." Journal of the American Chemical Society 140.8 (2018): 2919-2925. (Year: 2018).*
Liu 2018 Supplementary Materials (Year: 2018).*
Yuen, Alexander KL, and Craig A. Hutton. "Deprotection of pinacolyl boronate esters via hydrolysis of intermediate potassium trifluoroborates." Tetrahedron letters 46.46 (2005): 7899-7903. (Year: 2005).*

*Primary Examiner* — Sahana S Kaup
(74) *Attorney, Agent, or Firm* — OLSON & CEPURITIS, LTD.

(57) ABSTRACT

A high-throughput screening methods for identifying candidate anticancer medicinal agents is described herein. The candidate anticancer medicinal agents are arylfluorosulfate compounds derived from phenolic compounds. The method involves in situ generation of the arylfluorosulfate compounds in multi-well plates by reaction of phenolic compounds in DMSO with a saturated solution of $SO_2F_2$ dissolved in a solvent such as acetonitrile, in the presence of an organic base, followed by reaction of generated fluoride ion with trimethylsilanol to form volatile trimethylsilyl fluoride. Solvents, organic base, and silyl compounds are then removed, in vacuo, to afford the arylfluorosulfate compounds suitable for biological screening in cancer cell lines without further purification.

20 Claims, 13 Drawing Sheets

Related U.S. Application Data continuation-in-part of application No. 16/158,608, filed on Oct. 12, 2018, now Pat. No. 10,765,645, which is a division of application No. 15/316,742, filed as application No. PCT/US2015/034516 on Jun. 5, 2015, now Pat. No. 10,117,840.

(60) Provisional application No. 62/615,328, filed on Jan. 9, 2018, provisional application No. 62/008,925, filed on Jun. 6, 2014.

(51) Int. Cl.

| | | |
|---|---|---|
| *A61K 31/4245* | (2006.01) | |
| *A61K 31/4168* | (2006.01) | |
| *A61K 31/407* | (2006.01) | |
| *A61K 31/4045* | (2006.01) | |
| *A61K 31/40* | (2006.01) | |
| *A61K 31/397* | (2006.01) | |
| *A61K 31/198* | (2006.01) | |
| *A61K 31/197* | (2006.01) | |
| *A61K 31/14* | (2006.01) | |
| *C07K 2/00* | (2006.01) | |
| *C07D 295/26* | (2006.01) | |
| *C07D 295/185* | (2006.01) | |
| *C07D 295/088* | (2006.01) | |
| *C07D 277/82* | (2006.01) | |
| *A61K 47/54* | (2017.01) | |
| *C40B 30/06* | (2006.01) | |
| *C40B 30/04* | (2006.01) | |
| *C40B 50/08* | (2006.01) | |
| *C12N 5/09* | (2010.01) | |
| *C40B 40/04* | (2006.01) | |

(56) References Cited

\* cited by examiner

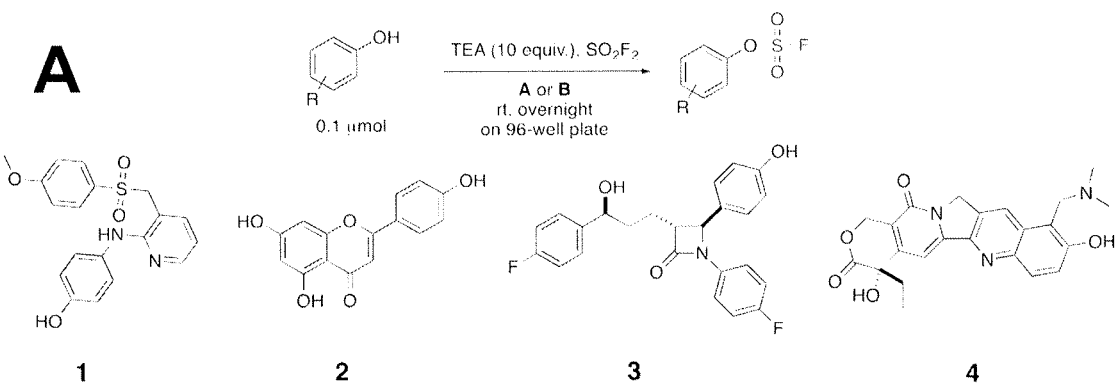

| COMPOUND NO. | A: SO$_2$F$_2$ gas | B: SO$_2$F$_2$ solution in CH$_3$CN* |
|---|---|---|
| 1 | 55%** | 84% |
| 2 | 24% | quant*** |
| 3 | 83% | quant |
| 4 | 63% | quant |

*: concentration ~4 mg/mL
**: All yields were determined by LC
***: quantitative yield

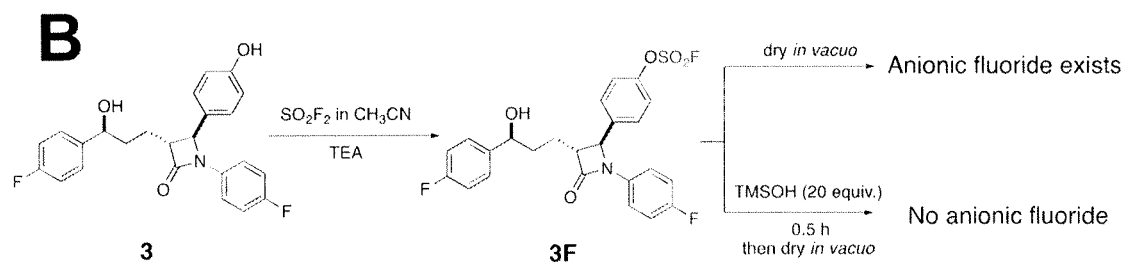

(1) Reaction crude → remove volatiles *in vacuo* overnight → $^{19}$F NMR in CDCl$_3$

Anionic fluorine (-151ppm)

(2) Reaction crude → TMSOH (20 equiv.), rt, 0.5h → remove volatiles *in vacuo* overnight → $^{19}$F NMR in CDCl$_3$

No anionic fluorine or TMSF

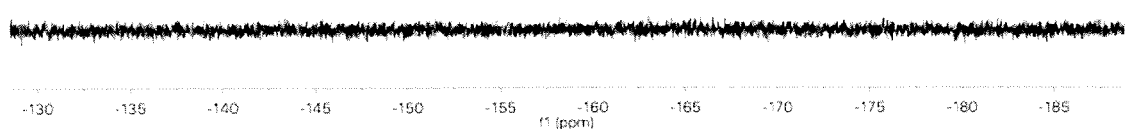

FIG. 2

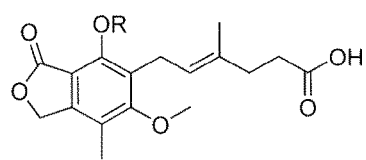
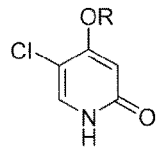
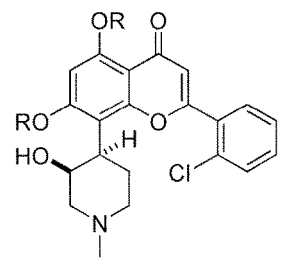
12F 72%   13F 88%   14F 70%
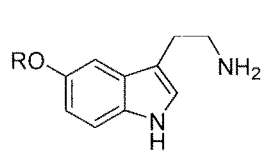
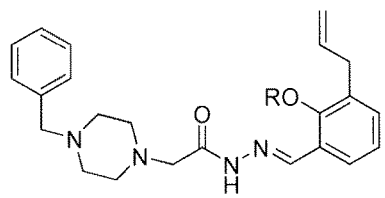
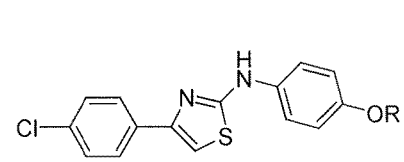
15F 50%   16F quant   17F quant
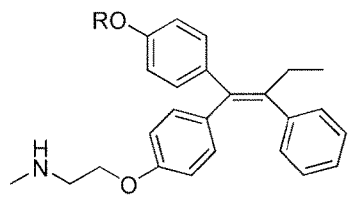
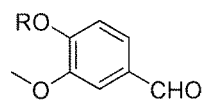
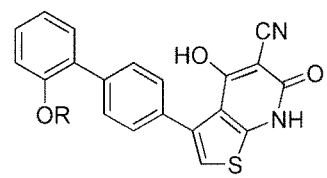
18F 88%   19F quant   20F 97%
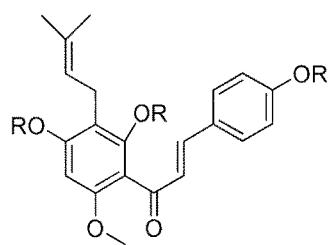
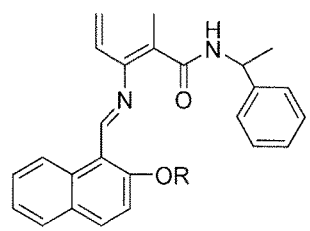
21F 48%   22F 72%
FIG. 8 (continued)

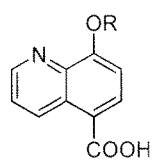
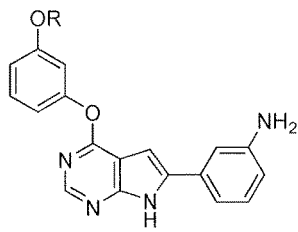
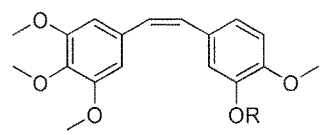
23F 73%          24F quant          25F quant
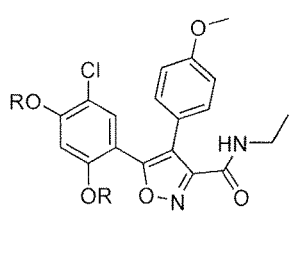
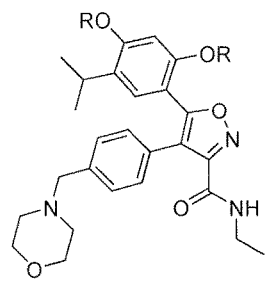
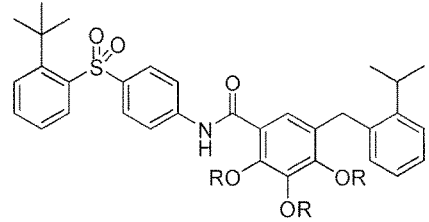
26F 56% (di) 40% (mono)     27F quant          28F 90%
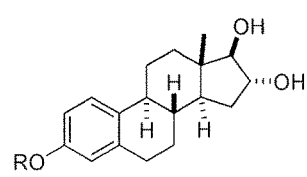
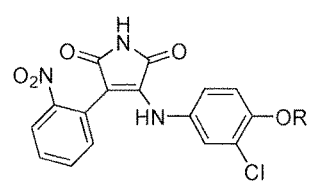
29F 66%          30F 99%
FIG. 8 (continued)

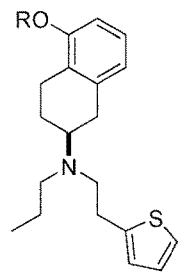 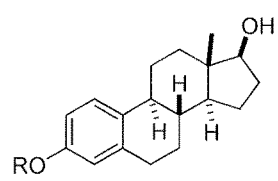 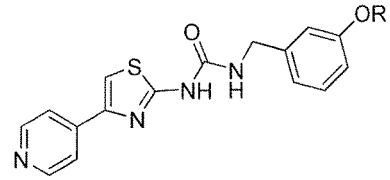
31F 74%　　　　　32F 56%　　　　　33F 98%
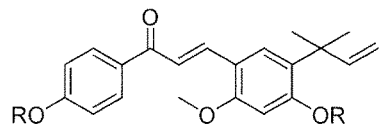 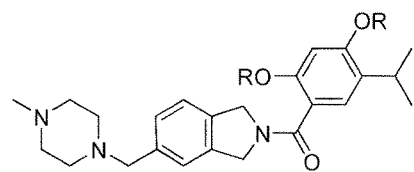 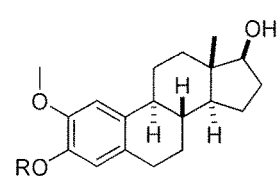
34F quant　　　　35F 97%　　　　　36F 53%
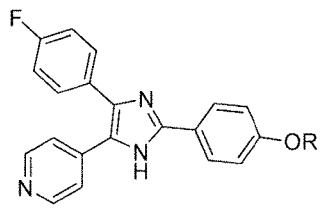 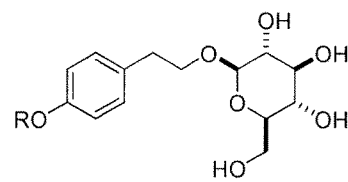 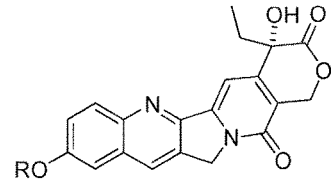
37F 92%　　　　　38F quant　　　　39F quant
FIG. 8 (continued)

ARYLFLUOROSULFATE COMPOUNDS AND METHODS

CROSS-REFERENCE TO RELATED APPLICATIONS

This application is a continuation of U.S. application Ser. No. 16/243,761, filed on Jan. 9, 2019, which is a continuation-in-part of U.S. application Ser. No. 16/158,608, filed on Oct. 12, 2018, which is a division of U.S. application Ser. No. 15/316,742, filed on Dec. 6, 2016, now U.S. Pat. No. 10,117,840, which is a 371 of PCT/US2015/034516, filed on Jun. 5, 2015, which claims the benefit of U.S. Provisional Application Ser. No. 62/008,925, filed on Jun. 6, 2014, each of which is incorporated herein by reference in its entirety. U.S. application Ser. No. 16/243,761, filed on Jan. 9, 2019, also claims the benefit of U.S. Provisional Application Ser. No. 62/615,328, filed on Jan. 9, 2018, which is incorporated herein by reference in its entirety.

STATEMENT OF GOVERNMENT SUPPORT

This invention was made with government support under R01GM117145 and R01GM111938 awarded by the National Institutes of Health. The government has certain rights in the invention.

BACKGROUND

Click chemistry, inspired by Nature's powerful heteroatom-linkage creation strategy, has found broad applications in materials chemistry, chemical biology, and drug development since the concept was first introduced in 1998. The sulfur (VI) fluoride exchange (SuFEx), developed by the Sharpless lab in 2014, represents another set of ideal click chemistry transformations. In SuFEx manifestation, arylfluorosulfates (Ar—O—SO$_2$—F) and iminosulfur oxydifluorides (R—N=SOF$_2$) can be readily synthesized using two gases sulfuryl fluoride (SO$_2$F$_2$) and thionyl tetrafluoride (SOF$_4$), respectively. Though rarely studied in the past, these two S(VI)-F motifs have since been successfully used as connective linkers in polymer synthesis and for the construction of various functional molecules.

However, due to the previous inaccessibility of these compounds and their assumed high reactivity toward biomolecules as is the case of other sulfur (VI) halides, the study and application of S(VI)-F in medicinal chemistry has largely been unexplored. In the Sharpless lab's pilot work with the Kelly group at the Scripps Research Institute, it was discovered that arylfluorosulfates are only reactive toward proximal nucleophilic residues, e.g. tyrosine, found within specific protein partners. These unique features make arylfluorosulfates distinct from other sulfur (VI) halides and herald an emerging invaluable tool in drug development.

There is an ongoing need to develop new drug candidates, particularly in the area of cancer treatment. The compounds and methods described herein address this need.

SUMMARY

Described herein is a method of SuFEx chemistry for the conversion of phenolic compounds to their respective arylfluorosulfate derivatives in situ in 96-well plates. This method is compatible with automated synthesis and screening to quickly assess the biological activities of the in situ generated crude products. Using this method, late-stage functionalization of a panel of known anti-cancer drugs generated the corresponding arylfluorosulfates. These in situ generated arylfluorosulfates were directly tested in a cancer-cell growth inhibition assay in parallel with their phenolic precursors. Three arylfluorosulfates exhibited improved anti-cancer cell proliferation activities compared to their phenol precursors (ABT-751, fulvestrant, and combretastatin A4). Among these compounds, the fluorosulfate derivative of fulvestrant showed significantly enhanced activity to down-regulate estrogen receptor (ER) expression in ER$^+$ breast cancer cell line MCF-7; and the fluorosulfate derivative of combretastatin A4 exhibited a 70-fold increase in potency in the drug resistant colon cancer cell line HT-29.

In one aspect, a fluorosulfate compound is provided, which comprises a fluorosulfate derivative of a phenolic medicinal agent, e.g., an anticancer agent, wherein at least one phenolic OH group of the medicinal agent is replaced by —OSO$_2$F. In some embodiments the medicinal agent is selected from the group consisting of ATB-751 (1), apigenin (2), ezetimibe (3), topotecan (4), ganetespib (5), etoposide (6), G100713 (7), estrone (8), PI-103 (9), raloxifene (10), fulvestrant (11), mycophenolic acid (12), gimeracil (13), flavopiridol (14), serotonin (15), PAC-1 (16), SKI II (17), endoxifen (18), vanillin (19), A-769662 (20), xanthohumol (21), sirtinol (22), IOX1 (23), TWS119 (24), combretastatin A4 (25), VER-50589 (26), luminespib (27), TW-37 (28), estrol (29), SB415286 (30), rotigotine (31), estradiol (32), RKI-1447 (33), licochalcone A (34), onalespib (35), 2-methoxyestrodiol (36), SB202190 (37), salidroside (38), 10-hydroxycamptothecin (39, 10-HCPT), lasofoxifene, lipid encapsulated 7-ethyl-10-hydroxycamptothecin, (LE-SN38), diethylstilbestrol, amrubicin, genistein, and phenoxodiol.

In one embodiment, a compound of Formula 1F is provided, which is a fluorosulfate derivative of ABT-751:

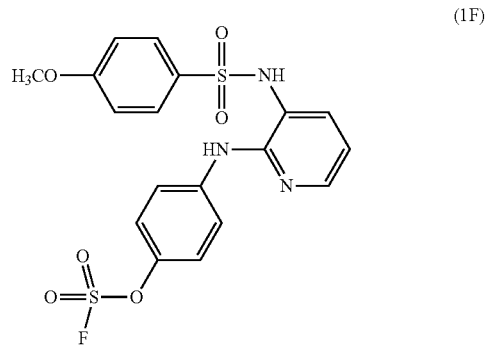 [SMILES: COc1ccc(S(=O)(=O)Nc2cccnc2Nc2ccc(OS(=O)(=O)F)cc2)cc1]

(1F)

which is a useful antimitotic agent for treating certain cancers, e.g., certain breast cancer. The parent, underivatized phenolic compound, ABT-751 reportedly binds to the colchicine site on beta-tubulin, which leads to a block in the cell cycle at the G2M phase, resulting in cellular apoptosis. Thus, ABT-751 has general activity against a variety of cancers and solid tumors, for example. Also disclosed herein is a method of treating a cancer in a patient (e.g., a human), comprising administering an effective dose of a compound of Formula 1F to the patient.

In another embodiment, a compound of Formula 11F is provided, which is a fluorosulfate derivative of fulvestrant:

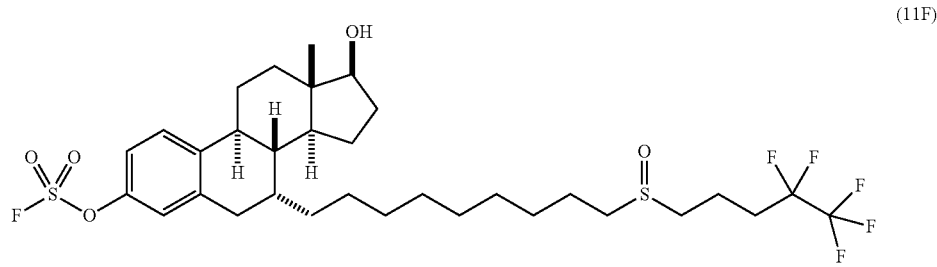

(11F)

and which is useful for treatment of certain cancers, e.g., certain breast cancers. Fulvestrant is indicated for the treatment of hormone receptor positive metastatic breast cancer in postmenopausal women with disease progression following antiestrogen therapy. However, this drug has poor bioavailability and the only administration method is through intramuscular injection at a dose of 250 mg/month. It takes over 3 months to reach a steady serum concentration due to its quick clearance, significantly limiting its clinical value. Also disclosed herein is a method of treating a cancer in a patient (e.g., a human), comprising administering an effective dose of a compound of Formula 11F to the patient.

In another embodiment, a compound of Formula 25F is provided, which is a fluorosulfate derivative of combretastatin A4:

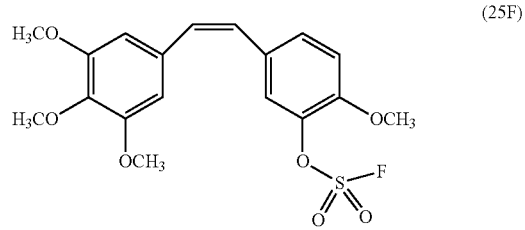 [SMILES: COc1ccc(/C=C\c2cc(OC)c(OC)c(OC)c2)cc1OS(=O)(=O)F]

(25F)

and which is useful for treatment of certain cancers, e.g., certain breast cancers. Combretastatin A-4 is a tubulin-binding chemotherapy drug that is structurally related to colchicine, and has general anti-cancer activity. Also disclosed herein is a method of treating a cancer in a patient (e.g., a human), comprising administering an effective dose of a compound of Formula 25F to the patient.

The foregoing fluorosulfate (O-fluorosulfonyl) derivatives were prepared by contacting the phenol compound with a solution of $SO_2F_2$ in acetonitrile at room temperature. The method is adapted for use with a compound library in a high throughput screening format, such as a multi-well plate, e.g., 32-, 64- or 96-well plates, each well containing a compound comprising a phenolic hydroxyl group, for conversion to the corresponding fluorosulfonyl derivative. This library of fluorosulfonylated compounds was then tested in various bioactivity evaluations.

The forgoing fluorosulfate compounds can be formulated into a pharmaceutical composition comprising the compound in a pharmaceutically acceptable carrier.

In another aspect, the fluorosulfate compounds can be utilized in a method of treatment of cancer in a patient (e.g., a human, or non-human animal), comprising administering an effective dose of the compound to the patient.

In yet another aspect, the foregoing fluorosulfate compounds can be used for preparing a medicament for treating cancer.

BRIEF DESCRIPTION OF THE FIGURES

FIG. 2 depicts development and optimization in situ SuFEx reaction and processing conditions. (A) comparison of gas-liquid based SuFEx and liquid based SuFEx protocols for reactions in 96 well plates; (B) removal of fluoride ions in situ after reaction: (1) volatiles in the reaction mixture were removed in vacuo, $^{19}F$ NMR showed the presence of anionic fluorine (−151 ppm, in $CDCl_3$); (2) after treating with trimethylsilanol (TMSOH), volatiles in the reaction mixture were removed in vacuo and $^{19}F$ NMR showed no presence of anionic fluorine or trimethylsilyl fluoride (TMSF).

Figure 5:
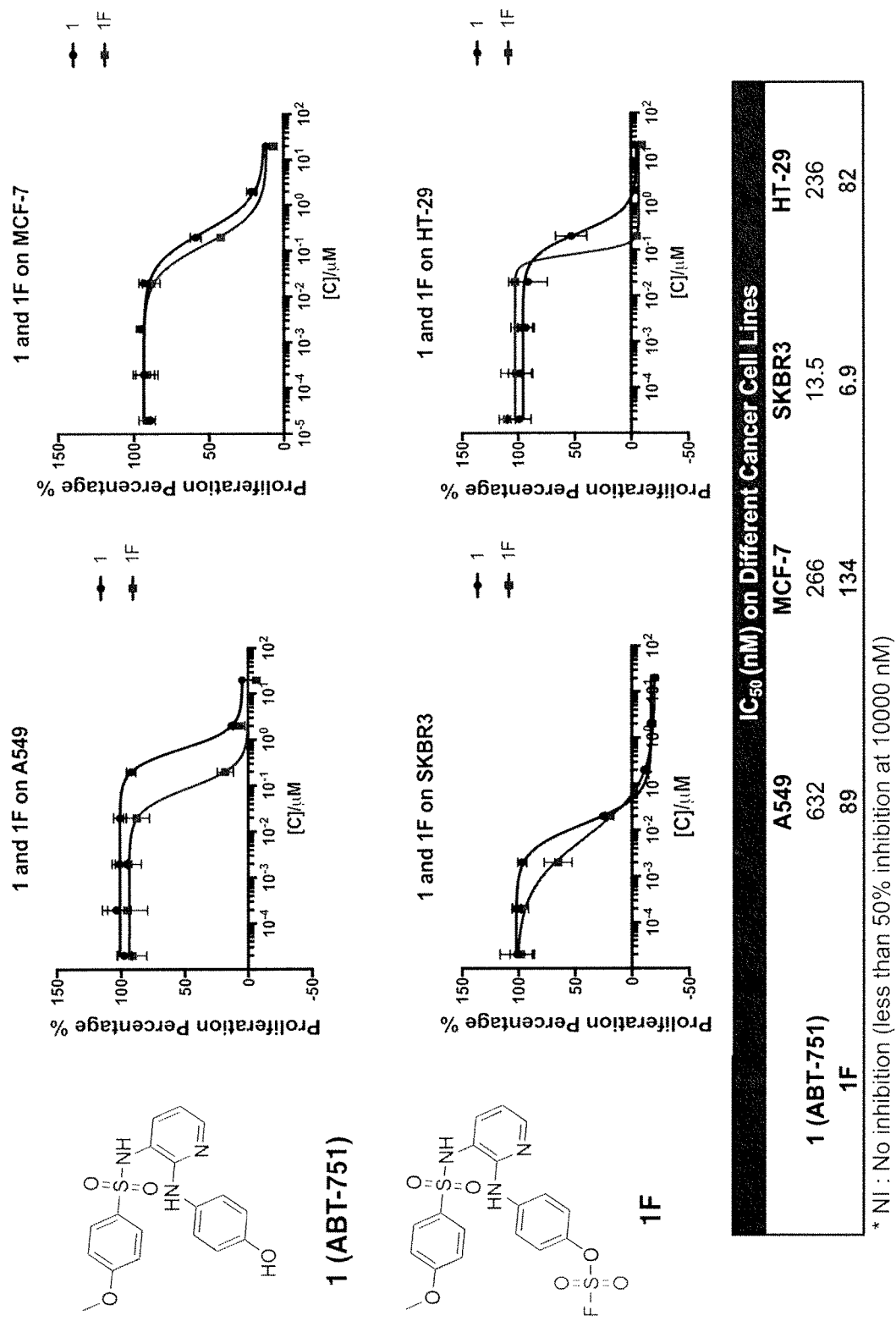

FIG. 5 provides proliferation inhibition curves of 1 and 1F on different cancer cell lines (n=3) at concentrations in the ranges of $2 \times 10^{-5}$ μM to 20 μM.

Figure 6:
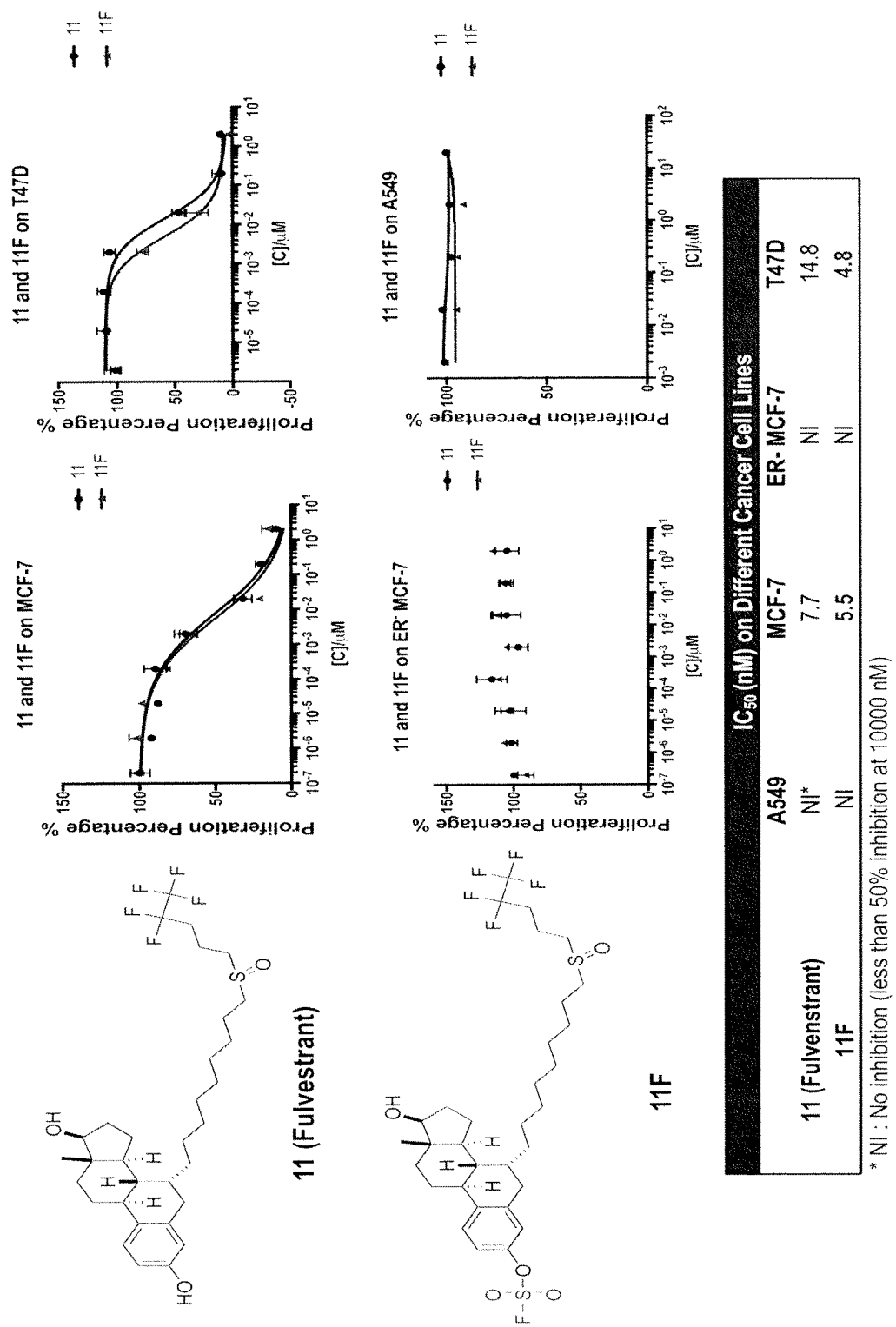

FIG. 6 provides proliferation inhibition curves of 11 and 11F on different cancer cell lines (n=3) at concentrations in the ranges of $2 \times 10^{-7}$ μM to 20 μM.

Figure 7:
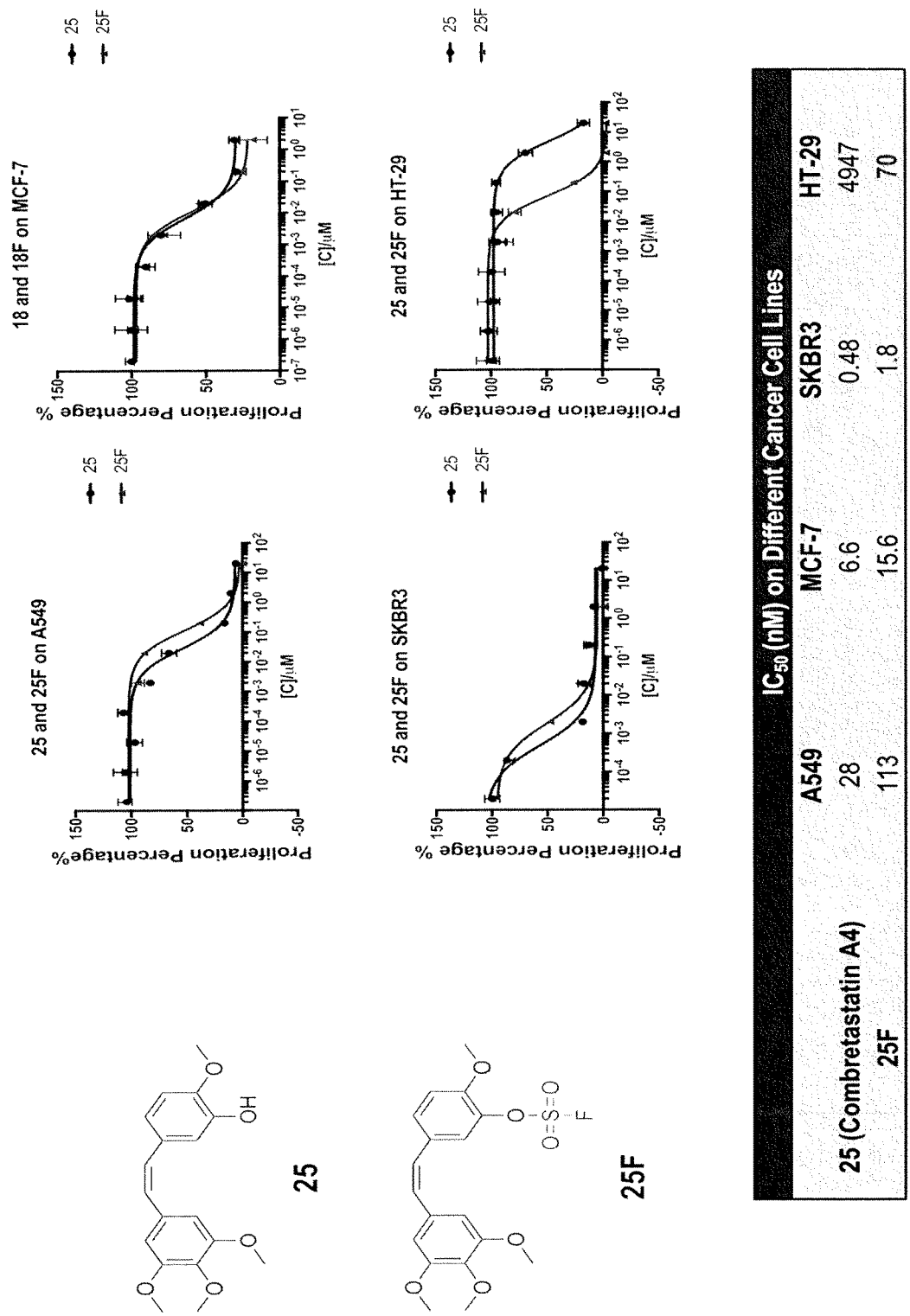

FIG. 7 provides proliferation inhibition curves of 25 and 25F on different cancer cell lines (n=3) at concentrations in the range of $2 \times 10^{-7}$ μM to 20 μM.

Figure 8:
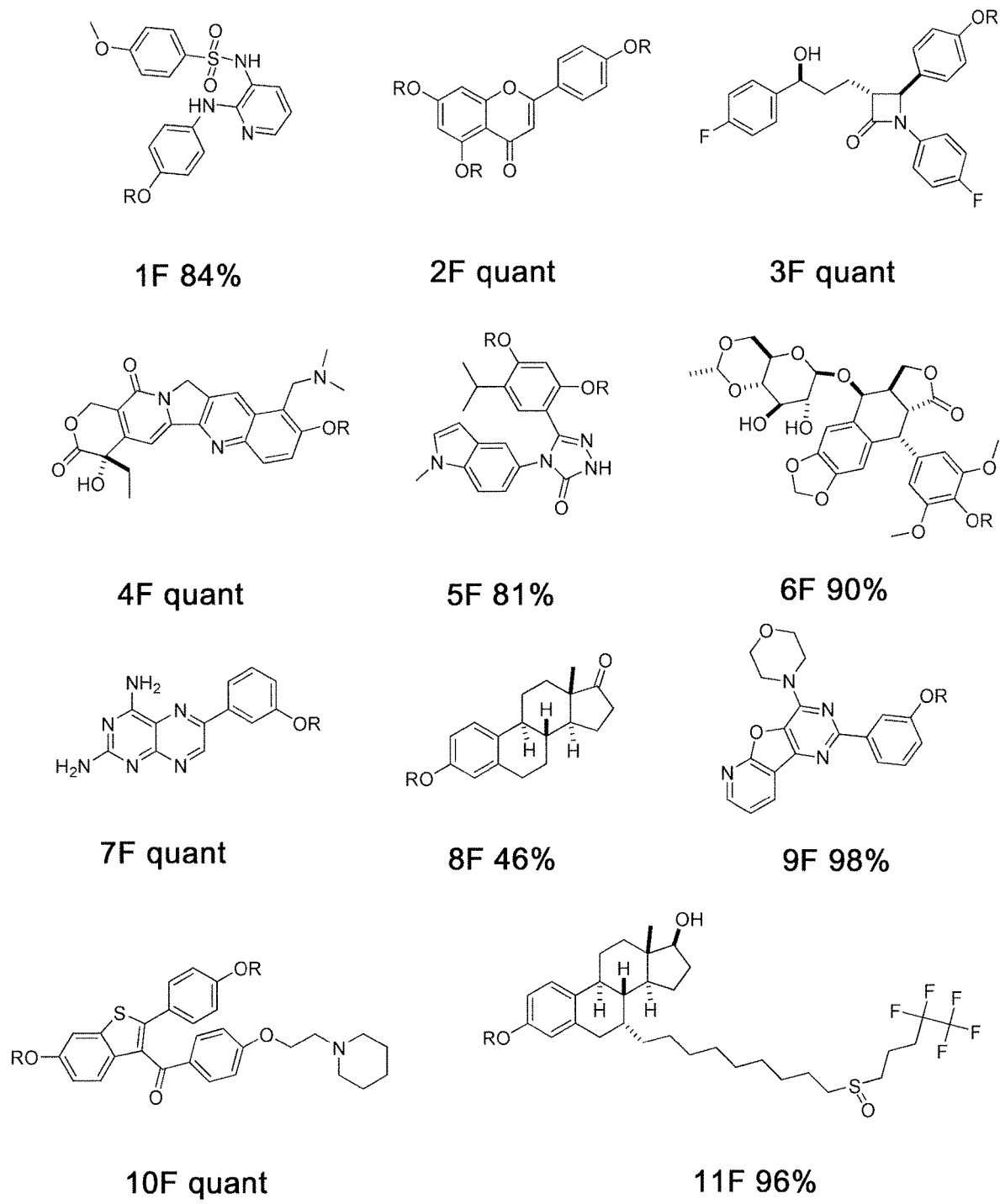

FIG. 8 depicts fluorosulfate derivatives prepared by in situ reaction of phenolic anticancer compounds with $SO_2F_2$ using the methods described herein.

Figure 9:
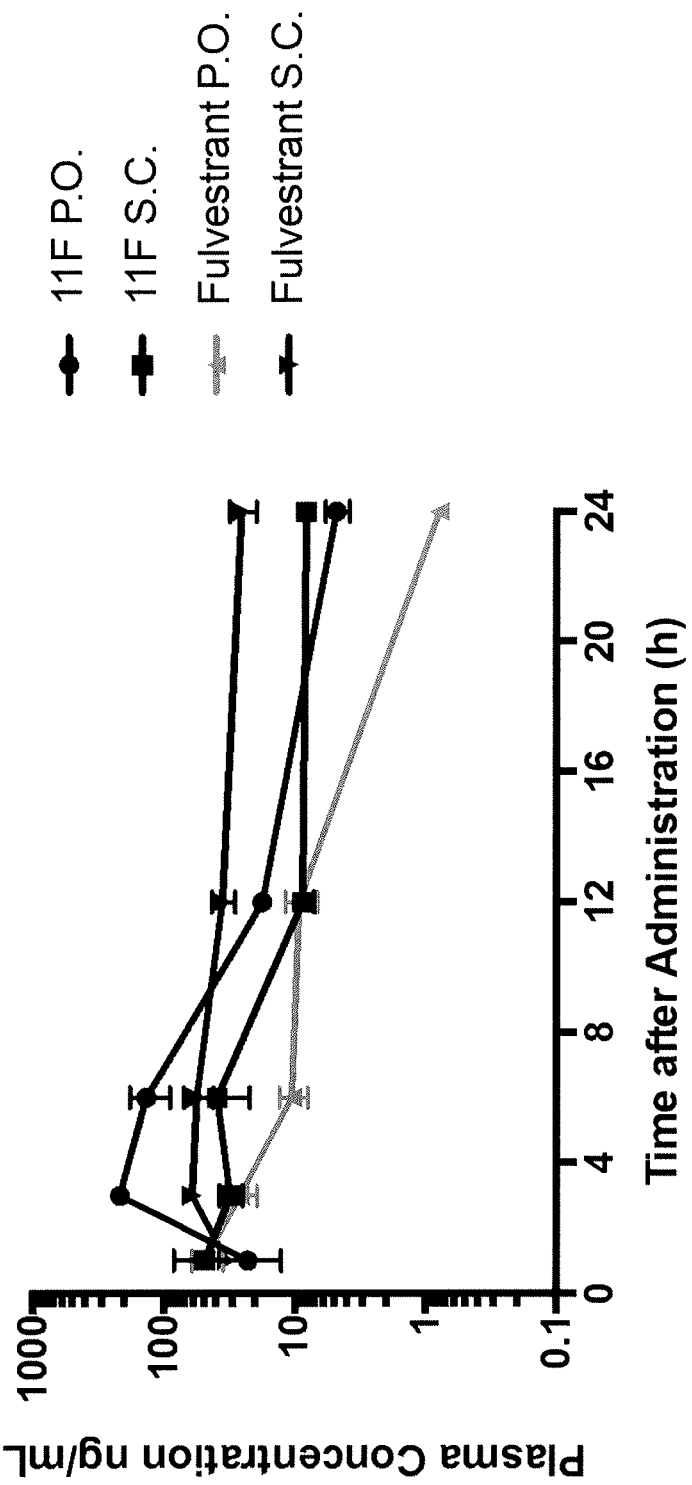

FIG. 9 shows a comparison of the PK profile of 11F and fulvestrant (11) following single P.O. or S.C. administrations to female C57BL/6 mice.

DETAILED DESCRIPTION

Late-stage functionalization (LSF), a strategy for directly introducing functional groups onto a bioactive compound in the late stage of its synthesis, enables rapid diversification of drug candidates or drug-like molecules to improve their properties such as potency and metabolic properties. Many innovative methods have been developed for this endeavor, including late stage C-H functionalization and nucleophilic aromatic substitution, just to name a few. LSF requires a chemical reaction with high selectivity, high yield and mild reaction conditions. Converting a phenolic compound with known biological activities to the corresponding fluorosulfate via SuFEx is an excellent transformation for LSF, which is waiting to be explored further. In fact, the phenolic hydroxyl group is often employed in drug modification and diversification. Converting a phenolic molecules with known biological activities to the corresponding fluorosulfate serves as a quick and cost-effective way to identify new hits with similar or even improved properties. Currently, there are approximately 120 phenolic compounds within the repertoire of FDA-approved drugs. In addition, hundreds of drug candidates bearing phenols are under investigation according to the Canadian online DrugBank database.

Current gas-liquid interface-based reaction protocols for the installation of arylfluorosulfates are hurdles for the direct transfer of SuFEx to the drug development pipeline. In a drug discovery process, compounds are usually tested using automated screening to quickly assess their biological activities, which requires a protocol to achieve the chemo-selective and efficient functionalization of screening compounds in situ in multi-well plates with low substrate concentrations and small volumes. Ideally compounds produced in such ways should be subjected to biological assays directly without further purification. The very nature of click chemistry, including high selectivity and yields with minimal byproducts as well as facile purification, provides an excellent solution to meet such requirement.

Figure 1:
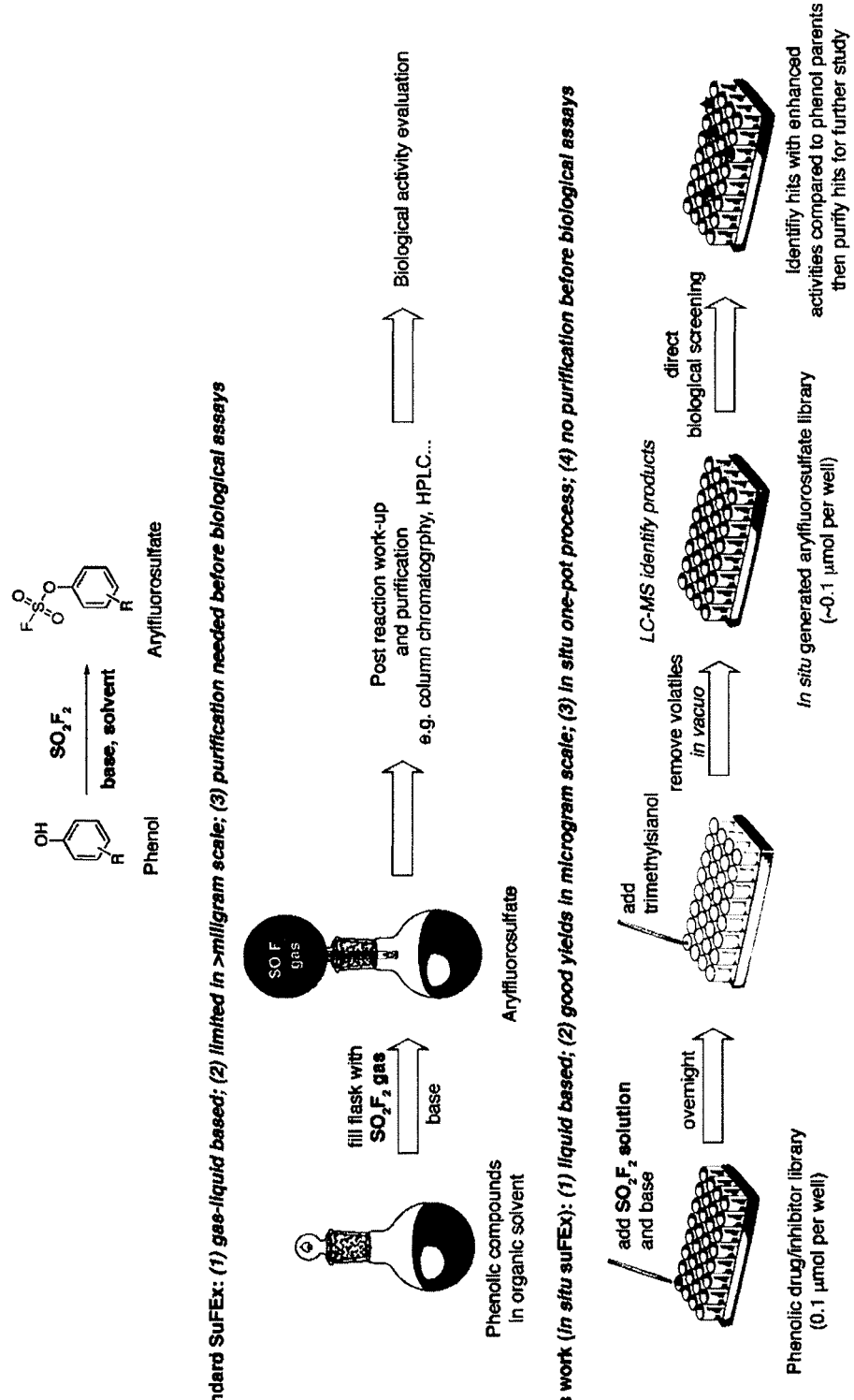
FIG. 1 provides a comparison of phenolic drug functionalization workflows via the standard SuFEx and in situ SuFEx reactions.

Described herein is a protocol of SuFEx click chemistry for the LSF of phenol-containing drugs or drug candidates for converting the phenolic hydroxyl groups thereof to their respective arylfluorosulfate derivatives in situ in multi-well (e.g. 96-well) plates (FIG. 1). The in situ generated crude products of arylfluorosulfates were directly tested in a cancer-cell growth inhibition assay together with their phenolic precursors. Three arylfluorosulfates exhibited improved anti-cancer proliferation activities compared to their phenol precursors. Among these compounds, the fluorosulfate derivative of combretastatin A4 exhibited a 70-fold increase in potency on the combretastatin-resistant colon cancer cell line HT-29.

Development of a Liquid-based in situ SuFEx Protocol.

As aforementioned, a cost-effective protocol for converting a commercial screening library into a new library should possess the following characteristics: (1) compatible with small reaction scales (e.g., microgram); (2) excellent chemoselectivity; and (3) directly transferable to biological assays. Currently, the typical procedure for synthesizing arylfluorosulfates is performed at the gas-liquid interface: phenol compounds dissolved in organic solvents (e.g., dichloromethane (DCM) or acetonitrile) are subjected to the $SO_2F_2$ gas in a sealed reaction vessel in the presence of an organic base (e.g. diisopropylethylamine (DIPEA)). This protocol is suitable for high concentration (>100 mM) reactions in which substrates are present in milligram or greater scales, but becomes impractical for low concentration samples (<10 mM) due to dramatically decreased reaction kinetics under such conditions.

To develop an in situ SuFEx procedure that can be easily coupled with LSF and quick biological assays, the feasibility of pre-dissolving $SO_2F_2$ in an organic solvent to form a saturated solution was explored for use in reacting phenolic compounds with $SO_2F_2$ in 96-well plates. Such a procedure is easily conducted by multichannel pipette or a robotic system. Indeed, $SO_2F_2$ is known to have good solubility in several organic solvents including carbon tetrachloride and toluene. Toward this end, saturated solutions of $SO_2F_2$ in various organic solvents (100 μL) were prepared and mixed with ezetimibe (3), a commercial phenol-containing drug (0.1 μmol in 10 μL dimethyl sulfoxide (DMSO)), in the presence of TEA or DIPEA (10 equiv., in 10 μL of the solvent) in a sealed Eppendorf™ tube at room temperature. The reaction progress was monitored by liquid chromatography-mass spectrometry (LC-MS). Reactions in $CH_3CN$ afforded significantly better yields after 3 hours (h) compared to those obtained by using DCM or THF as the solvent.

Next, the efficiency of the interfacial and the liquid-based method was compared in a 96-well plate. Phenol compounds 1, 2, 3, and 4 (0.1 μmol) were treated with either $SO_2F_2$ atmosphere over an open 96-well plate, or by addition of a dissolved $SO_2F_2$ solution (about 4 mg/mL in $CH_3CN$) in a sealed 96-well plate for 12 h (a total volume of 120 μL in each well). All substrates achieved higher yields in the liquid-based system compared to the gas-liquid based method (>20% increase) (FIG. 2, A).

Unlike low boiling point solvents and organic bases, fluoride ions generated in this transformation cannot be removed by vacuo (−151 ppm in $CDCl_3$; FIG. 2, B). Fluoride ions may have a synergistic or detrimental effect on arylfluorosulfates in the downstream biological assay. To minimize such influence on the screening results, excess trimethylsilanol (TMSOH, 20 equiv., boiling point 99° C. at 1 atm) was used to convert fluoride ions into volatile trimethylsilyl fluoride (TMSF, −158 ppm in $CDCl_3$) whose boiling point is 16° C. at 1 atm. The subsequent in vacuo treatment could then remove nearly all low boiling point components (TMSF, TMSOH, and TEA), leaving behind only a small amount of unreacted phenol precursors and the arylfluorosulfate products, which could be directly used for the subsequent biological screening tests (FIG. 2, B).

Using this liquid-based protocol in a 96-well plate, thirty-nine fluorosulfate derivatives (0.1 μmol) were obtained in good to quantitative yields, whose parent phenolic compounds (FIG. 8) all possess anti-cancer activities. In FIG. 8, R is —SO₂F for the fluorosulfate derivatives, whereas R is H for the parent phenolic drugs. The phenol compounds are numbered as 1 to 39 and the corresponding fluorosulfate derivatives are designated 1F to 39F. In FIG. 8, estimated yields for the in situ fluorosulfation reactions are provided after derivative compound numbers, where "quant" means quantitative yield. Notably, some of the compounds bearing multiple phenolic hydroxyl groups (fluorosulfate derivatives 5, 10, 27 and 37) were fully transformed into the corresponding fluorosulfation products (i.e., all phenolic OH groups reacted). In the case of reaction of compound 28, only one of the three phenolic OH groups reacted (as determined by LC-MS), thus in compound 28F, two of the R groups are H. In the case of compound 2, only two of the three phenolic OH groups reacted. Due to the small quantities involved, and subsequent biological testing, the identities of the unreacted OH groups in 2F and 28F were not determined. Similarly, reaction of compound 26 resulted in a mixture of mono and di-fluorosulfation. Compounds 18 and 34 (as well as 18F and 34F), were mixtures of E/Z isomers. This approach also is applicable to a wide range of substrates and high chemoselectivity: phenol rings bearing electron-withdrawing and electron-donating groups are both reactive with $SO_2F_2$. Finally, the crude products were dissolved in DMSO (10 μL; approximately 10 mM) for the direct evaluation of their anti-cancer activities. The common names of the underivatized drugs used to form fluorosulfate derivatives 1F-39F are: 1 (ATB-751), 2 (apigenin), 3 (ezetimibe), 4 (topotecan), 5 (ganetespib), 6 (etoposide), 7 (G100713), 8 (estrone), 9 (PI-103), 10 (raloxifene), 11 (fulvestrant), 12 (mycophenolic acid), 13 (gimeracil), 14 (flavopiridol), 15 (serotonin), 16 (PAC-1), 17 (SKI II), 18 (endoxifen), 19 (vanillin), 20 (A-769662), 21 (xanthohumol), 22 (sirtinol), 23 (IOX1), 24 (TWS119), 25 (combretastatin A4), 26 (VER-50589), 27 (luminespib), 28 (TW-37), 29 (estrol), 30 (SB415286), 31 (rotigotine), 32 (estradiol), 33 (RKI-1447), 34 (licochalcone A), 35 (onalespib), 36 (2-methoxyestrodiol), 37 (SB202190), 38 (salidroside), and 39 (10-HCPT). Additional FDA approved anticancer drugs that are suitable for derivitization with sulfonyl fluoride in the same manner include lasofoxifene, diethylstilbestrol, LE-SN38, amrubicin, genistein, and phenoxodiol. Fluorosulfate derivatives of such compounds also can be utilized in the treatment of the same cancers as the parent compounds.

The fluorosulfate compounds described herein can be formulated as a pharmaceutical composition in combination with a pharmaceutically acceptable carrier (also referred to as a vehicle or diluent). Such carriers are well known in the pharmaceutical arts, and include, e.g., solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

In the present specification, the phrase "effective dose" means the amount of the subject compound that will elicit the biological or medical response of a tissue, system or animal, (e.g. mammal or human) that is being sought by the researcher, veterinarian, medical doctor or other clinician. The compounds described herein are administered in therapeutically effective dose to treat a disease. Alternatively, an effective dose of a compound is the quantity required to achieve a desired therapeutic and/or prophylactic effect.

Screening the Anti-Cancer Activity of the In Situ SuFEx Generated 1F to 39F.

Figure 3:
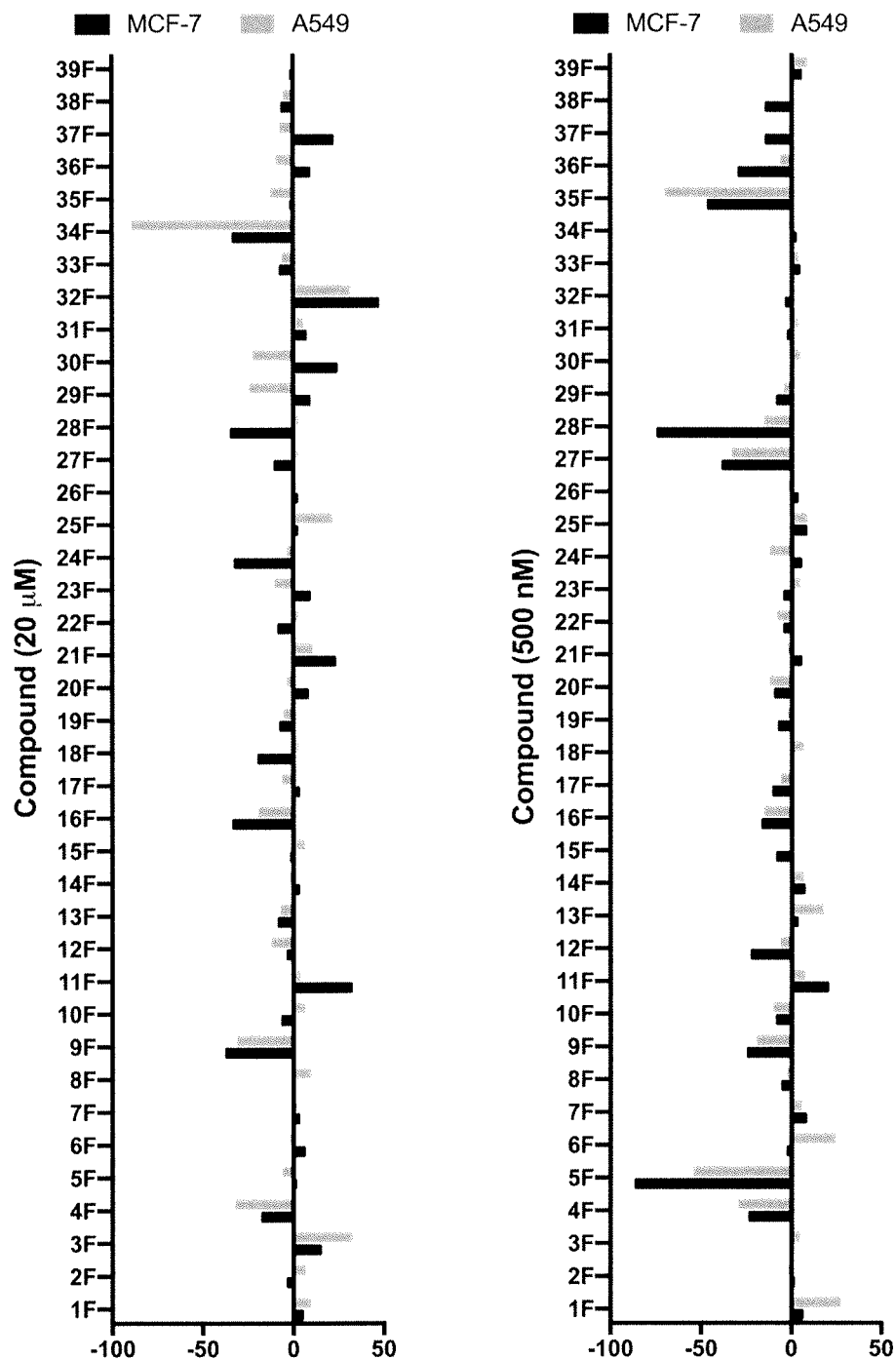
FIG. 3 shows cytotoxicity profiling of the in situ generated fluorosulfate derivatives 1F to 39F using a double-dose cell-viability assay; (A) thirty-nine in situ SuFEx generated fluorosulfation products 1F to 39F were tested in a cell-viability assay with MCF-7 and A549 cells at the final concentrations of 20 μM and 500 nM. After a 72-hour treatment, the cytotoxicity of fluorosulfate derivatives 1F to 39F and their phenol precursors 1 to 39 were evaluated according to the cancer cell viabilities relative to vehicle (DMSO) control. Bar graphs reflect the % increase or decrease of the cytotoxicity of the corresponding fluorosulfation product compared to its phenol precursor (n=3); (B) cancer cell viabilities under the treatment of in situ generated fluorosulfate derivatives 1F, 11F and 25F and their phenol parents at a final concentration of 20 μM and 500 nM for 72 hours. Cells treated with dimethylsulfoxide (DMSO; 0.2%) as the vehicle control. The structures of fluorosulfate derivatives 1F, 11F and 25F were confirmed by nuclear magnetic resonance after flash column chromatography purification. P values were calculated using two-way ANOVA (n=3); ns: P≥0.05; *: P≤0.1; : P≤0.01; *: P≤0.001; ****: P≤0.0001.
Figure 3:
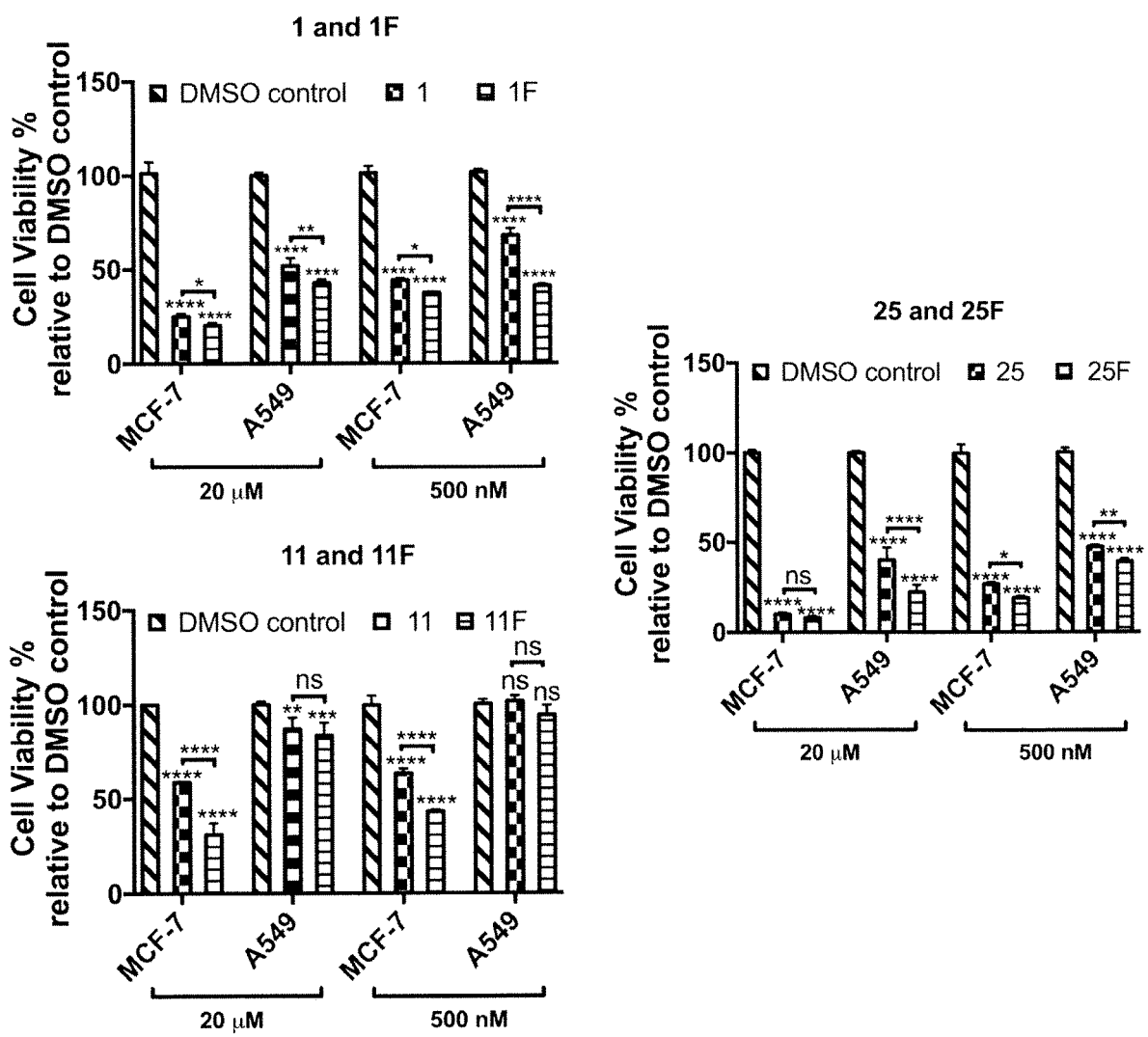

The cytotoxicity of fluorosulfation products 1F to 39F and their phenol precursors was assessed in cancer cell lines using a double-dose cell viability test. The adenocarcinomic human alveolar basal epithelial cell A549 and the breast cancer cell MCF-7 were treated with vehicle (0.2% DMSO), fluorosulfation products or their phenol precursors in a final concentration of 20 μM or 500 nM for 72 h before the cytotoxicity of each compound was assessed according to the viability of cancer cells relative to the vehicle control. The difference between the cytotoxicity of a fluorosulfation product and that of its phenol precursor reflects the changes in compounds' anti-cancer activity after the SuFEx-based derivatization (FIG. 3, A). A fluorosulfation product exhibiting strong cytotoxicity (cell viability relative to the vehicle control less than 50% at both 20 μM and 500 nM on MCF-7 or A549 after a three-day treatment) and significantly increased (>10%) cytotoxicity over the parent compound is considered as a "hit". Based on these two selection criteria, three hits 1F, 11F and 25F, were identified. As shown in FIG. 3, B, fluorosulfate derivative 1F exhibited significantly enhanced activity relative to phenol precursor 1 at 500 nM (6% on MCF-7 and 27% on A549). The cytotoxicity of fluorosulfate derivative 11F was stronger than that of phenol 11 on MCF-7 cell line with an increase of 32% and 20%, respectively, at 20 μM and 500 nM. However, no significant differences were found on A549 cells. Although phenol 25 and fluorosulfate derivative 25F showed similar activities on MCF-7 cells at 20 μM, fluorosulfate derivative 25F indeed exhibited 8% enhanced cytotoxicity at 500 nM, and its activities are significantly stronger than those of 25 at both concentrations on A549 cells. Notably, the corresponding phenol precursors 1, 11 and 25 are either FDA-approved drugs or are currently under clinical trials. Specifically, 1 (ABT-751), which inhibits polymerization of microtubules, is under a phase1/2 clinic trial; 11 (fulvestrant) is the only selective estrogen receptor down regulator (SERD) for the treatment of $ER^+$ metastatic breast cancer in postmenopausal women whose disease has spread after anti-estrogen therapy; and 25 (combretastatin A4) is a naturally occurring stilbenoid found in plants with activity in a wide range of cancers. The corresponding phosphate of combretastatin A4 is a tumor vascular targeting agent, and the water-soluble prodrug of combretastatin A4.

$IC_{50}$ Evaluation of 1F, 11F and 25F on Cancer Cell Lines.

To quantitatively compare the potency of 1F, 11F and 25F with their parent phenolic drugs, we synthesized and purified these compounds in gram quantities and determined their $IC_{50}$ values on a panel of cancer cell lines.

The anti-tumor potencies of arylfluorosulfate 1F and its phenol precursor 1 were evaluated against lung cancer cell line A549, breast cancer cell line MCF-7, SKBR3 and colon cancer cell line HT-29. As shown in Table 1, compound 1 showed $IC_{50}$ of 632 nM, 266 nM, 13.5 nM and 236 nM on A549, MCF-7, SKBR3 and HT-29 cells, respectively. In comparison, 1F exhibited 2 to 5-fold lower $IC_{50}$ values on these three cancer cell lines, i.e., 89 nM on A549, 134 nM on MCF-7, 6.9 nM on SKBR3 and 82 nM on HT-29. Similarly, 11F exhibited strong inhibition of the proliferation of $ER^+$ breast cancer cell lines MCF-7 and T47D, with $IC_{50}$ values of 5.5 nM and 4.8 nM, respectively, which are at the same level with those of 11 (7.7 nM and 14.8 nM, respectively) (Table 1). In addition, both 11 and 11F have no activity on $ER^-$ MCF-7 and lung cancer A549 cells, suggesting 11F may still target estrogen receptors. Although the measured $IC_{50}$ values of arylfluorosulfate 25F on A549, MCF-7, and SKBR3 cells were slightly higher compared to those of its parent drug 25 (Table 1), compound 25F showed stronger activities to inhibit these three cells at high concentrations (20 μM and 2 μM) according to dose-response studies, which is consistent with the two-dose screening results (FIG. 3). Surprisingly, the $IC_{50}$ value of 25F on HT-29 cells, a drug resistant colon cancer cell line, is 70 nM, which is 70-fold lower than the $IC_{50}$ of compound 25 (4,947 nM). After confirming the anti-tumor potency of these three compounds, two of them (11F and 25F) were selected for further mechanistic studies.

TABLE 1

$IC_{50}$ values (nM) of arylfluorosulfate derivatives and their phenol precursors on different cancer cell lines.

| Compound | IC50 (nM) | | | |
| --- | --- | --- | --- | --- |
| | A549 Cells | MCF-7 Cells | SKBR3 Cells | HT-29 Cells |
| 1 (ABT-751) | 632 | 266 | 13.5 | 236 |
| 1F | 89 | 134 | 6.9 | 82 |
| 11 (fulvestrant) | NI | 7.7 | NI | 14.8 |
| 11F | NI | 5.5 | NI | 4.8 |
| 25 (combretastatin A4) | 28 | 6.6 | 0.48 | 4947 |
| 25F | 113 | 15.6 | 1.8 | 70 |

NI: No Inhibition (i.e., less than 50% inhibition at 10000 nM)

Fluorosulfate 11F is a New SERD with Strong Potency.

Figure 4:
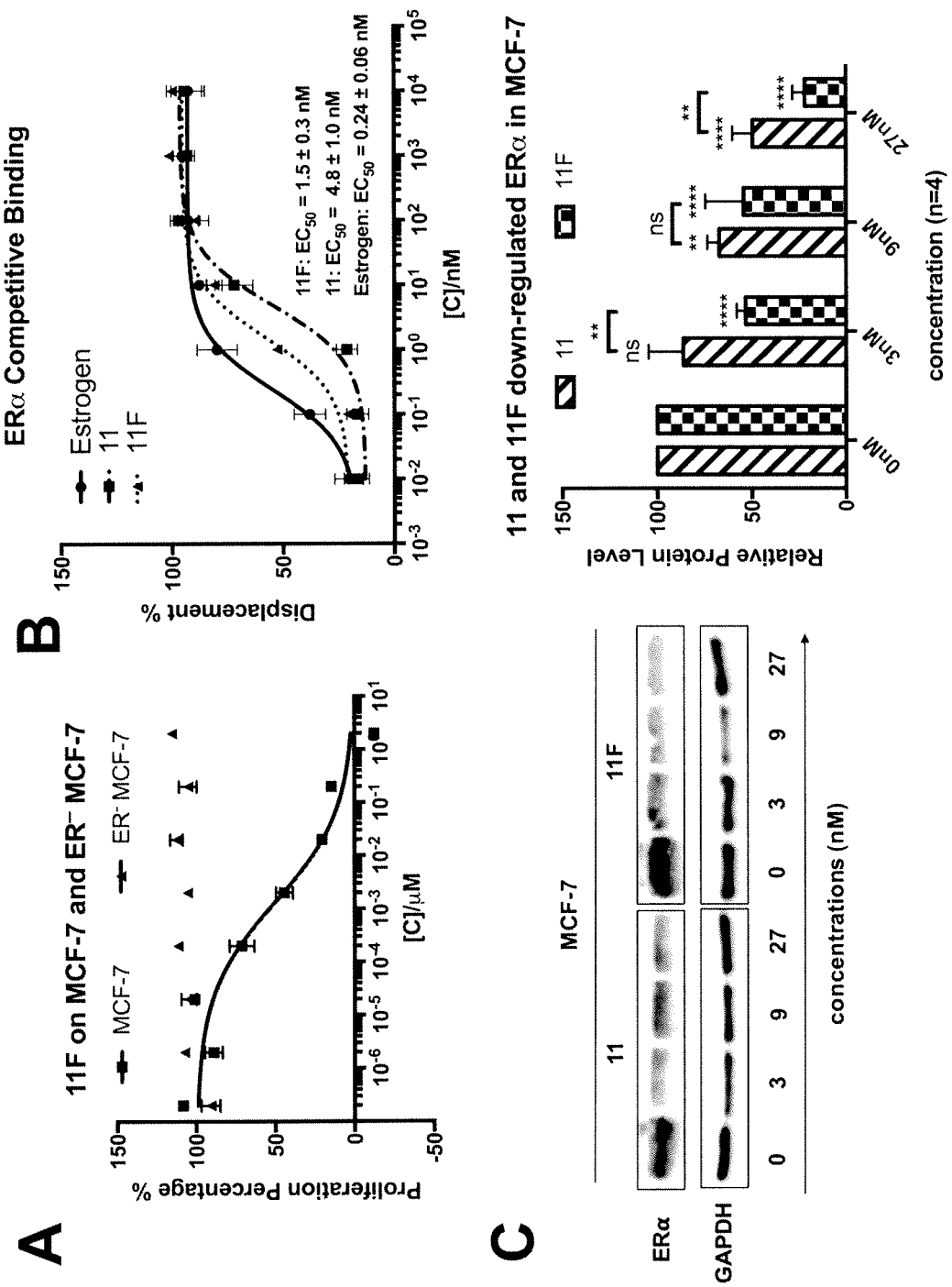
FIG. 4 demonstrates that fluorosulfate derivative 11F is a new selective estrogen receptor degrader or downregulator (SERD) that binds to and down-regulates Estrogen Receptor; (A) fluorosulfate derivative 11F specifically inhibits the proliferation of $ER^+$ MCF-7 cells; (B) competitive binding curves of Estrogen, fulvestrant (11) and fluorosulfate derivative 11F to ERα evaluated by a PolarScreen™ ERα competitor assay kit from Life Technologies (n=3); (C) compounds 11 and 11F induce ER down-regulation in MCF-7 cells. P values were calculated using two-way ANOVA. n=4; ns: P≥0.05; *: P≤0.1; : P≤0.01; *: P≤0.001; ****: P≤0.0001.

Since fluorosulfate derivative 11F has stronger anti-cancer potency than the commercial drug 11, the cellular target of this new compound was investigated to determine whether it shares the same cellular target with compound 11. As described previously, fulvestrant (11) is the only SERD on the market for the treatment of $ER^+$ breast cancer. Fulvestrant competitively binds to estrogen receptor, which is a crucial regulator of $ER^+$ breast cancer growth, inhibiting dimerization of ER and leading to its degradation. As shown in FIG. 4, A, fluorosulfate 11F inhibited $ER^+$ MCF-7 proliferation, but had no effect on $ER^-$ MCF-7 cells, suggesting that the anti-cancer activity of 11F is still ER dependent.

A competitive displacement ER binding assay, in which the binding affinity of 11 and 11F to ERα protein was compared in competition with a fluoromone ligand was performed to confirm that ER is the target of fluorosulfate 11F. Notably, fluorosulfate 11F binds to ERα with a relative $EC_{50}$ of 1.5 nM, which is 3-fold stronger than that of fulvestrant ($EC_{50}$=4.8 nM) (FIG. 4, B). Finally, to determine whether 11F was capable of downregulating the ERα expression level, MCF-7 cells were treated with 11 or 11F at concentrations of 3 nM, 9 nM, or 27 nM for 5 days. The ERα expression levels of the treated cells were then determined by Western blot. Both 11 and 11F downregulated ERα in a dose dependent manner, and 11F showed significantly stronger ERα down-regulation activity (FIG. 4, C). These results confirm that 11F acts as a SERD with strong potency. New SERDs with improved bioavailability are needed. In a recent report, Wang et al. demonstrated that the phenol moiety in 11 could be converted into a borate in a 5-step synthesis. The resulting compound has excellent bioavailability regardless of slightly weaker potency. The cause of its improved bioavailability is believed to derive from blocked phase II metabolism in the blood stream, which is consistent with the finding that fluorosulfate 11F showed surprisingly good oral bioavailability in vivo in C57BL/6 mice, whereas fulvestrant (11) is not effectively orally absorbed (FIG. 9). Importantly, fluorosulfate 11F can be synthesized from 11 using a one-step quantitative "click" procedure, making it readily accessible for the future pharmacokinetics evaluation in animal models.

Fluorosulfate 25F Overcomes the Drug Resistance of HT-29.

Combretastatin A4 (25) is a one of the most potent anti-vascular agents that targets the colchicine-binding site of β-tubulin and hence disrupts tubulin polymerization. To assess the mechanism of fluorosulfate 25F, HT-29 cells were treated with 25F followed by staining with anti-tubulin-FITC antibody. Confocal imaging revealed that HT-29 cells treated with a vehicle (0.2% DMSO) or combretastatin A4 (25) at various concentrations clearly showed the presence of the microtubule network. Surprisingly, cells treated with fluorosulfate 25F (1 μM and 0.1 μM) for 24 h completely lost microtubule structure, consistent with tubulin depolymerization. Previous investigations of the in vitro and in vivo phase II metabolism revealed that 25 is rapidly converted into the corresponding glucuronide and sulfate metabolites via glucuronidation and sulfation, respectively. In fact, glucuronidation of 25 on the phenol group by uridine 5-diphosphoglucuronosyl transferases (UGTs) has been previously identified as a mechanism of resistance evolved by HT-29 colon cancer cells and hepatocellular cancer cells. Indeed, the expression level of UGT1 in HT-29 cells is significantly higher than those of non-drug-resistant A549 and MCF-7 cells. Combined together, the above observations indicate that 25F inhibits microtubule formation and surprisingly overcomes combretastatin A4 (25) resistance in HT-29 cells.

FIGS. 5, 6, and 7 show results of proliferation inhibitions studies in cancer cell lines. The data in the figures show improved activity for the fluorosulfate derivatives relative to the underivatized drug in at least one cell line and dosage level. Without being bound by theory, it is believed that converting a phenol group into an arylfluorosulfate is unlikely to change the protein targeting specificity of the parent compound, but instead this transformation confers the resulting arylfluorosulfate new properties which may enact in distinct mechanisms. In some cases an arylfluorosulfate forms a covalent bond with the target protein via $S^{VI}$-F exchange given the presence of tyrosine residues in the binding pocket and the presence of residues to facilitate the F departure. In other cases, a fluorosulfate-containing molecule binds to its target via non-covalent interactions stronger than that of the parent phenolic compound, which in some cases blocks the phase II metabolism pathway of the phenol moiety, i.e. sulfation, glucuronidation, and oxidation, which are key routes that change the pharmacokinetic properties of a phenolic compound.

All patents and publications referred to herein are incorporated by reference herein to the same extent as if each individual publication was specifically and individually indicated to be incorporated by reference in its entirety.

EXAMPLES

General $^1$H NMR spectra were recorded at 400 MHz on Bruker™ AV-400 NMR spectrometers; $^{13}$C NMR were recorded at 151 MHz on Bruker™ AV-600. $^{19}$F NMR were recorded at 376 MHz on Bruker™ AV-400. All chemical shifts (δ) are quoted in ppm; coupling constants (J) in hertz. Tetramethylsilane was used as international reference for $^1$H and $^{13}$C NMR. Trichlorofluoromethane was used as international reference for $^{19}$F NMR. Abbreviations are: s, singlet; d, doublet; t, triplet; q, quartet, p, pentet; br s, broad singlet; m, multiplet. Liquid chromatography-mass spectrometry (LC-MS) was performed on an Agilent™ 1260 LC/MSD with an Agilent™ 6120 quadrupole mass spectrometer (electrospray ionization, ES) eluting with 0.05% trifluoroacetic acid in H$_2$O and 0.05% trifluoroacetic acid in CH$_3$CN. Precoated Merck™ F-254 silica gel plates were used for thin layer analytical chromatography (TLC) and visualized with short wave (254 nm) UV light or by potassium permanganate stain. Column chromatography was performed using Silicycle™ Silica Gel 60 (40-63 μm). All phenol compounds were purchased from Selleck chemicals. Sulfuryl fluoride (SO$_2$F$_2$) gas was a gift from Dow AgroSciences. Phenolic compound library (10 mM in DMSO) was purchased from Selleck Chemicals.

Example 1. Preparation of Sulfuryl Fluoride (SO$_2$F$_2$) Solution in Organic Solvent A glass vial of organic solvent (5 mL) was evacuated in vacuo and a balloon containing SO$_2$F$_2$ gas was connected with the glass vial, filling the vial with gas. Then the organic solvent was vigorously stirred for 30 min to make the stock solution of sulfuryl fluoride.

Example 2. Condition Screening for In Situ SuFEx

A solution of SO$_2$F$_2$ in organic solvent (CH$_3$CN, DCM or THF, 100 μL) and base (triethylamine (TEA) or diisopropylethylamine (DIPEA)), 1 μmol in 10 μL corresponding organic solvent) were added in an Eppendorf™ tube containing compound 3 (0.1 μmol in 10 μL DMSO). The tube was sealed by parafilm and left at room temperature for 3 hours before the product and yield was evaluated by LC-MS.

Example 3. General Procedure I for the Gas/Liquid Based SuFEx Method on a 96-Well Plate CH$_3$CN (100 μL) and TEA (1 μmol in 10 μL CH$_3$CN) were added in each well of a 96-well plate containing phenol compounds (0.1 μmol in 10 μL DMSO). The plate was left without lid in a vacuum desiccator containing SO$_2$F$_2$ (~1 atm) at room temperature overnight, before the products and yields were evaluated by LC-MS.

Example 4. General Procedure II for the Liquid Based SuFEx Method on a 96-Well Plate A solution of SO$_2$F$_2$ in CH$_3$CN (~4 mg/mL, 100 μL) and TEA (1 μmol in 10 μL) were added in each well of a 96-well plate containing phenol compounds (0.1 μmol in 10 μL DMSO). The plate was left tightly covered by a solvent resistant sealing mat (Corning™ 96 well storage system) at room temperature overnight. Then trimethylsilanol (2 μmol in 10 μL CH$_3$CN) was added to each well and left for 0.5 hours before the plate was left in vacuo overnight. The resulting crudes were dissolved in DMSO (10 μL, ~10 mM) before biological assays. The products and yields were determined by LC-MS.

Example 5. Synthesis of 1F, 11F and 25F in Milligram Scale for IC$_{50}$ Evaluation 5A. 4-((3-((4-Methoxyphenyl)sulfonamido)pyridin-2-yl)amino)phenyl sulfurofluoridate 1F

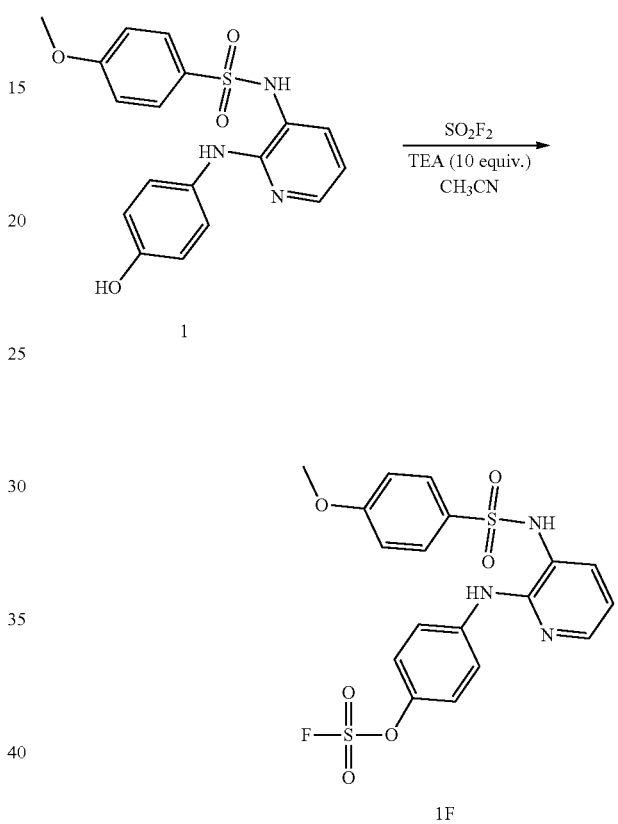

Triethylamine (TEA) (27.2 mg, 0.27 mmol) was added in a solution of compound 1 (10 mg, 0.027 mmol) in CH$_3$CN (0.5 mL). After evacuation, SO$_2$F$_2$ gas was back-filled in the flask and the reaction mixture was left with stirring at room temperature for 12 hours until TLC (hexane/ethyl acetate, 1:1) showed the full conversion of starting material 1 to 1F (R$_f$ 0.70). Then volatiles were removed in vacuo and the resulting crude product was purified by flash column chromatography (hexane/ethyl acetate, 2:1 to 1:2) to obtain fluorosulfate 1F (11.3 mg, 0.025 mmol, 93%) as a light red solid.

m.p. 158° C.-160° C.; $^1$H NMR (400 MHz, CDCl$_3$): 8.15 (dd, 1H, J=4 Hz, 8 Hz), 7.67 (t, 4H, J=8 Hz), 7.26 (d, 2H, J=8 Hz), 6.94 (d, 2H, J=8 Hz), 6.81 (dd, 1H, J=4 Hz, 8 Hz), 6.63 (dd, 1H, J=4 Hz, 8 Hz), 3.85 (s, 3H); $^{13}$C NMR (151 MHz, CDCl$_3$): 164.0, 153.0, 147.4, 144.6, 140.8, 136.8, 130.2 (2C), 129.5, 121.6 (2C), 120.5 (2C), 118.1, 115.8, 114.7 (2C), 56.0; $^{19}$F NMR (376 MHz, CDCl$_3$): 36.1; ESI (m/z): 454 [M+H]$^+$.

5B. (7R,8R,9S,13S,14S,17S)-17-Hydroxy-13-methyl-7-(9-((4,4,5,5,5-pentafluoropentyl)sulfinyl)nonyl)-7,8,9,11,12,13,14,15,16,17-decahydro-6H-cyclopenta[a]phenanthren-3-yl sulfurofluoridate 11F

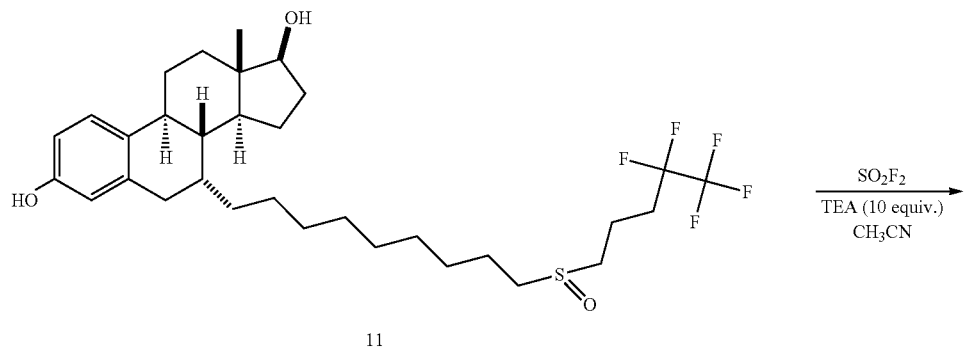

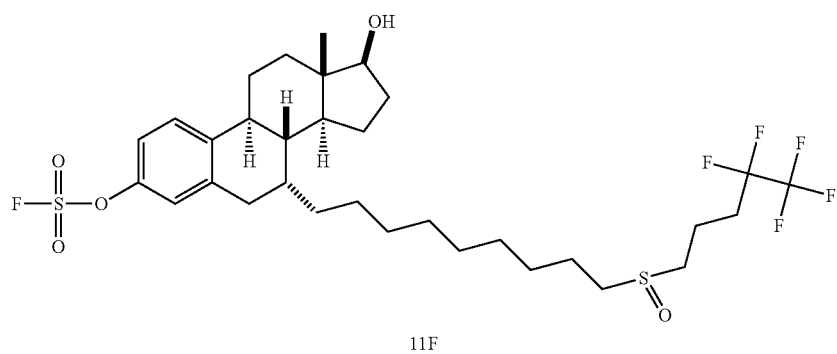

Triethylamine (TEA) (41.5 mg, 0.41 mmol) was added in a solution of compound 11 (25 mg, 0.041 mmol) in CH$_3$CN (0.5 mL). After evacuation, SO$_2$F$_2$ gas was back-filled in the flask and the reaction mixture was left with stirring at room temperature for 1 hours until TLC (hexane/ethyl acetate, 1:1) showed the full conversion of starting material 11 to 11F (R$_f$ 0.40). Then volatiles were removed in vacuo and the resulting crude product was purified by flash column chromatography (hexane/ethyl acetate, 5:1 to 1:2) to obtain fluorosulfate 11F (25.5 mg, 0.037 mmol, 90%) as a colorless foam.

$^1$H NMR (400 MHz, CDCl$_3$): 7.37 (d, 1H, J=8 Hz), 7.09 (d, 1H, J=8 Hz), 7.03 (s, 1H), 3.76 (t, 1H, J=12 Hz), 2.93 (dd, 1H, J=8 Hz, 16 Hz), 2.82-2.59 (m, 5H), 2.40-2.13 (m, 7H), 1.95 (d, J=12 Hz), 1.80-1.72 (m, 3H), 1.65-1.59 (m, 4H), 1.53-1.19 (m, 20H), 0.98 (br s, 1H); $^{13}$C NMR (151 MHz, CDCl$_3$): 148.4, 140.8, 139.0, 128.3, 121.9, 118.0, 82.2, 53.0, 51.3, 46.8, 43.6, 41.8, 38.6, 37.1, 34.9, 33.3, 30.9, 30.2, 30.0, 29.9, 29.8, 29.7, 29.5, 29.1, 27.4, 28.4, 26.0, 23.0, 22.92, 22.91, 15.0, 11.4; $^{19}$F NMR (376 MHz, CDCl$_3$): 37.2, −85.7, −118.05 to −118.64 (m); ESI (m/z): 689 [M+H]$^+$.

5C. (Z)-2-Methoxy-5-(3,4,5-trimethoxystyryl)phenyl sulfurofluoridate 25F

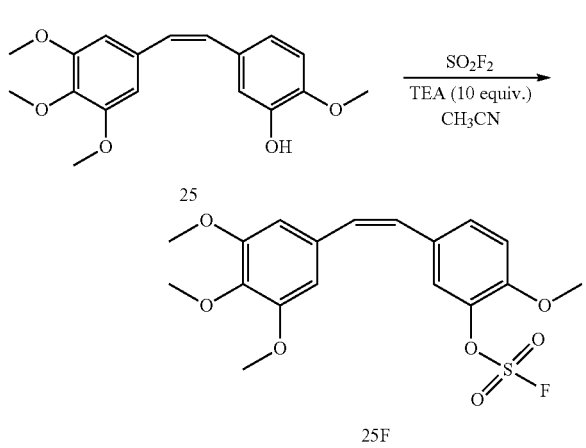

Triethylamine (TEA) (79.9 mg, 0.79 mmol) was added in a solution of compound 25 (25 mg, 0.079 mmol) in $CH_3CN$ (0.5 mL). After evacuation, $SO_2F_2$ gas was back-filled in the flask and the reaction mixture was left with stirring at room temperature for 2 hours until TLC (hexane/ethyl acetate, 1:1) showed the formation of product 25F ($R_f$ 0.86). Then solvent was removed in vacuo and the resulting crude product was purified by flash column chromatography (hexane/ethyl acetate, 5:1 to 1:1) to obtain fluorosulfate 25F (28.7 mg, 0.072 mmol, 91%) as a light-yellow syrup.

$^1$H NMR (400 MHz, $CDCl_3$): 7.26 (d, 1H, J=4 Hz), 7.24 (d, 1H, J=4 Hz), 7.19 (br s, 1H), 6.93 (d, 1H, J=8 Hz), 6.57 (d, 1H, J=12 Hz), 6.46 (d, 1H, J=12 Hz), 6.43 (s, 2H), 3.89 (s, 3H), 3.84 (s, 3H), 3.70 (s, 6H); $^{13}$C NMR (151 MHz, $CDCl_3$): 153.6, 150.4, 150.3, 138.9, 138.8, 137.8, 132.3, 131.3, 130.8, 130.6, 127.8, 123.0, 113.3, 106.0 (2×C), 61.3, 56.6, 56.2 (2×C); $^{19}$F NMR (376 MHz, $CDCl_3$): 39.5; EI (m/z): 399 [M+H]$^+$.

Example 6. In Vitro Biology

6A. Reagents and Software.

All culture media are purchased from GIBCO. Charcoal-stripped FBS, PolarScreen™ ERα competitor assay kit (Green) and CellTiter-Glo™ assay kit are purchased from Life Technologies. Mouse monoclonal anti-tublin-FITC antibody (DM1A) is from AbCam Inc. Rabbit monoclonal UGT1 antibody is from Cell Signaling Technology. Rabbit monoclonal ERα antibody is from AbCam Inc. Experimental data were processed by Prism 7™ and western blot images were analyzed by ImageJ 1.50i™ software.

6B. Cell Culture.

The MCF-7, A549, SKBR3 and HT-29 cells were originally purchased from ATCC. The T47D and ER$^-$ MCF-7 cells were kind grifts from Christopher K. Glass group (UCSD). All cancer cell lines were routinely maintained in DMEM (+Gluta MAX™) supplement with 10% FBS and 1% peneciline/streptomycin in 5% carbon dioxide at a temperature of 37° C.

6C. Two-Dose Cell Viability Assay to Compare the Cytotoxicities of Fluorosulfation Products (1F to 39F) and Phenol Parents (1 to 39).

All cancer cells for the anti-cancer assay were grown in DMEM (+Gluta MAX™) supplement with 5% FBS. MCF-7 and A549 cancer cells were inoculated into 96-well plates in 100 µL medium at a plating density of 5,000 cells/well. After cell inoculation, the plates were incubated at 37° C. and 5% $CO_2$. After 24 hours, all wells were refreshed with medium containing DMSO (0.2%, as vehicle control), phenols (20 µM or 500 nM) or in situ generated fluorosulfation products (20 µM or 500 nM). Then cancer cells were maintained at 37° C. and 5% $CO_2$ for 72 hours before cell viability ($V_{control}$, $V_{phenol}$ and $V_{fluorosulfation\ product}$) were evaluated by CellTiter-Glo™ Assay following manual of protocol. Cell viability percentage relative to vehicle control is defined as $V_{phenol}/V_{control} \times 100\%$ or $V_{fluorosulfation\ product}/V_{control} \times 100\%$. The cytotoxicity difference between a fluorosulfation product and its phenol precursor is quantified as ($V_{phenol}/V_{control} \times 100\%$)−($V_{fluorosulfation\ product}/V_{control} \times 100\%$).

6D. Cancer Cell Growth Inhibition Assay.

Experimental compounds were dissolved in DMSO at 500-fold of the desired final maximum test concentration. Then it was 10-fold serially diluted to other concentrations in DMSO. All aliquots were frozen prior to use. At the time of test, the aliquots of frozen concentrates are thawed and diluted to the desired final test concentrations with DMEM (+Gluta MAX™) supplement with 5% FBS.

6D(i). Growth Inhibition of MCF-7, A549, SKBR3 and HT-29 by 1 and 1F

All cancer cells for the anti-cancer assay were grown in DMEM (+Gluta MAX™) supplement with 5% FBS. Cancer cells were inoculated into a 96-well plate in 100 µL medium at a plating density of 5,000 cells/well. Another same plate of cells was inoculated for the evaluation of time 0. After cell inoculation, the plates were incubated at 37° C. and 5% $CO_2$ for 24 hours. Then the viabilities of cancer cells for time-0 were evaluated by CellTiter-Glo™ assay following manual of protocol to obtain $V_0$. And another plate of cancer cells was refreshed with medium containing either DMSO (0.2%, as control) or test compounds (1 or 1F) in seven different concentrations from 20 µM. After incubation for 72 hours, cell viabilities were evaluated by CellTiter-Glo™ assay to obtain $V_{control}$ and $V_{test}$. The growth inhibition percentage is defined as $(V_{test}-V_0)/(V_{control}-V_0) \times 100\%$. $IC_{50}$ values were obtained from dose-response curves. All tests included 3 repeats.

6D(ii). Growth Inhibition of MCF-7, T47D, ER$^-$ MCF-7 and A549 by 11 and 11F

All cancer cells for the anti-cancer assay were grown in DMEM (+Gluta MAX™) supplement with 5% charcoal-stripped FBS and 0.01 nM 17β-estradiol. Cancer cells were inoculated into a 96-well plate in 100 µL medium at a plating density of 3,000 cells/well. Another same plate of cells was inoculated for the evaluation of time 0. After cell inoculation, the plates were incubated at 37° C. and 5% $CO_2$ for 24 hours. Then the viabilities of cancer cells for time 0 were evaluated by CellTiter-Glo™ assay following manual of protocol to obtain $V_0$. Another plate of cancer cells was refreshed with medium containing either DMSO (0.2%, as control) or test compounds (11 or 11F) in 5 to 8 different concentrations from 20 µM (2 µM for MCF-7 and T47D cells). Then cells were incubated for 6 days with one change of medium containing test compounds on day 3, before cell viabilities were evaluated by CellTiter-Glo™ Assay to obtain $V_{control}$ and $V_{test}$. The growth inhibition percentage is defined as $(V_{test}-V_0)/(V_{control}-V_0) \times 100\%$. $IC_{50}$ values were obtained from dose-response curves. All tests included 3 repeats.

6D(iii). Growth Inhibition of MCF-7, A549, SKBR3 and HT-29 Using 25 and 25F

All cancer cells for the anti-cancer assay were grown in DMEM (+Gluta MAX™) supplement with 5% FBS. Cancer cells were inoculated into a 96-well plate in 100 µL medium at a plating density of 5,000 cells/well. Another same plate of cells was inoculated for the evaluation of time 0. After cell inoculation, the plates were incubated at 37° C. and 5% $CO_2$ for 24 hours. Then the viabilities of cancer cells for time 0 were evaluated by CellTiter-Glo™ assay to obtain $V_0$. Another plate of cancer cells was refreshed with medium containing either DMSO (0.2%, as control) or test compounds (25 or 25F) in 7 to 9 different concentrations from 20 µM (2 µM for MCF-7 cells). Then cells were incubation for 72 hours, before cell viabilities were evaluated by CellTiter-Glo™ assay to obtain $V_{control}$ and $V_{test}$. The growth inhibition percentage is defined as $(V_{test}-V_0)/(V_{control}-V_0) \times 100\%$. $IC_{50}$ values were obtained from dose-response curves. All tests included 3 repeats.

6E. ER Binding Assay.

Estrogen receptor binding assays were preformed using a PolarScreen™ ERα competitor assay kit (green) from Life Technologies following manual of protocol. This method uses recombinant ER and competition with a fluoromone ligand. The experiment included seven concentrations of test compounds from $10^4$ nM to $10^{-2}$ nM and three repeats for each concentration. Relative $EC_{50}$ values were obtained from dose-response curves.

6E(i). Western Blot for ERα Downregulation.

MCF-7 cells were inoculated in a 6-well plate at a seeding density of 10,000 cells/well in DMEM (+Gluta MAX™) supplement with 5% FBS. After incubation for 24 hours, cells were exposed to either 11 or 11F at the concentrations of 0 nM (0.2% DMSO), 3 nM, 9 nM and 27 nM for 5 days with daily changes of media containing test compounds. Then cells were lysed and stored at −80° C. until western blot for ERα. After cell lysis, denaturing and centrifuge at 20,000 rpm for 20 min, protein samples in equal volume were subjected to western protocol. Membranes were blocked and then incubated with 1:400 dilution of ERα antibody at 4° C. overnight followed by 1:5000 dilution of secondary antibody for 1 h at room temperature. GAPDH was detected as loading control. They were then imaged on a ChemiDoc™ imaging system (Bio-Rad).

6E(ii). Western Blot for UGT1 Expression on A549, MCF-7 and HT-29 Cells.

A549, MCF-7 and HT-29 cells were inoculated in a 6-well plate at a seeding density of 100,000 cells/well in DMEM (+Gluta MAX™) supplement with 5% FBS. After incubation for 24 hours, cells were incubated for 24 hours before cells were lysed and stored at −80° C. until western blot for UGT1. After cell lysis, denaturing and centrifuge at 20,000 rpm for 20 min, protein samples in equal volume were subjected to western protocol. Membranes were blocked and then incubated with 1:500 dilution of UGT1 antibody at 4° C. overnight followed by 1:5000 dilution of secondary antibody for 1 h at room temperature. GAPDH was detected as loading control. They were then imaged on a ChemiDoc™ imaging system (Bio-Rad).

6E(iii). Immunofluorescence Microscopy of HT-29 Microtubule Disruption Induced by 25 and 25F.

HT-29 were inoculated in a 4-well chamber at a seeding density of 10,000 cells/well in DMEM (+Gluta MAX™) supplement with 5% FBS. After incubation at 37° C. for 24 hours, cells were treated with media containing DMSO (0.2%), 25 (1 μM, 0.1 μM) or 25F (1 μM, 0.1 μM, 0.01 μM) for 24 hours. Then cells were gently washed in PBS, fixed for 20 min with 4% paraformaldehyde in PBS and permeabilised in 0.5% Triton X-100™ surfactant. Following washes in PBS containing 0.1% Tween™ (PBST) surfactant, cells were blocked in 5% bovine serum albumin diluted in PBST. Then cells were incubated with mouse monoclonal anti-tublin-FITC antibody (DM1A) (1:100 in PBS) for 3 hours. After washing with PBST, cells were incubated with DAPI (1:2000) for 30 min and mounted in PBS for confocal analysis. Images were captured by Nikon™ spinning disk confocal microscopy. All images in each experiment were collected on the same day using identical parameters.

Example 7. In Vivo Biology of Fulvestrant and Fluorosulfate 11F

The pharmacokinetic (PK) profiles of fulvestrant (11) and fluorosulfate derivative 11F were evaluated in female C57BL/6 mice using single oral (P.O.) or subcutaneous (S.C.) administrations of the compounds in 5% corn oil+5% DMSO. Results are summarized in FIG. 9.

Administration: P.O.: 8.3 mg/kg (10 mL/kg) via oral gavage (N=3); S.C.: 8.3 mg/kg (10 mL/kg) via subcutaneous injection (N=3).

Blood Collection and LC-MS: The mice were restrained manually at the designated time points, approximately 110 μL of blood sample was collected via retro-orbital puncture or cardiac puncture for terminal bleeding under the anesthesia with Isoflurane inhalation into K2EDTA tubes. The blood samples were maintained in wet ice first and centrifuged to obtain plasma (2000 g, 4° C., 5 min) within 15 minutes post sampling. Compound concentrations in plasma were determined by LC-MS.

Result Analysis: A comparison of the PK profile of 11F and fulvestrant (11) is shown in FIG. 9. The PK parameters are shown in Table 2. Fluorosulfate 11F showed surprisingly good oral bioavailability: Maximum plasma concentration (218 ng/mL) was reached in 3 hours post administration. In contrast, fulvestrant cannot be effectively absorbed orally with AUC 250 h·ng/mL. The half-life of 11F is around 4 h, which is lower than fulvestrant via S.C. (16.5 h). However, its Area Under Curve value (AUC) is 1380 h·ng/mL, which is higher than fulvestrant via S.C. (936 h·ng/mL). Fluorosulfate 11F showed lower bioavailability via S.C. administration.

TABLE 2

PK Parameters for fulvestrant and fluorosulfate derivative 11F.

| PK parameters | Unit | 11F P.O. | 11F S.C. | Fulvestrant P.O. | Fulvestrant S.C. |
|---|---|---|---|---|---|
| $T_{max}$ | h | 3 | 1 | 1 | 3 |
| $C_{max}$ | ng/mL | 218 | 48.7 | 48.6 | 61.6 |
| $T_{1/2}$ | h | 3.95 | 9.51 | 3.2 | 16.5 |
| AUC | h · ng/mL | 1380 | 455 | 250 | 936 |

What is claimed is:

1. A high-throughput screening method for identifying anticancer medicinal agents comprising an arylfluorosulfate functional group, the method comprising the sequential steps of:
   (a) distributing solutions of phenolic compounds into wells of a first multi-well plate with one phenolic compound per well, wherein each phenolic compound comprises one or more OH substituent on an aromatic moiety;
   (b) adding to each well of said first multi-well plate an organic base and a saturated solution of $SO_2F_2$, thereafter sealing each well, thereby initiating reactions between said OH substituents of the phenolic compounds with the $SO_2F_2$ and forming candidate arylfluorosulfate anticancer agents therefrom;
   (c) adding trimethylsilanol to each well in the first multi-well plate after the reaction in step (b) is complete to convert fluoride ion formed from the reaction of the phenolic compound and the $SO_2F_2$ into trimethylsilyl fluoride;
   (d) evaporating, in vacuo, solvents, the organic base, and trimethylsilyl compounds present in the wells to leave a residue of a candidate arylfluorosulfate anticancer agent in each well;
   (e) dissolving each residue in dimethylsulfoxide to form solutions of the candidate arylfluorosulfate anticancer agents;
   (f) adding selected concentrations of the candidate arylfluorosulfate anticancer agent solutions from step (e) to cancer cell cultures distributed in wells of a second multi-well plate;
   (g) incubating the cell cultures in the second multi-well plate under conditions suitable for viability or growth of the cancer cells; and (h) assessing the effect of the candidate arylfluorosulfate anticancer medicinal agents on the viability or growth of the cancer cells.

2. The method of claim 1, wherein the solutions in step (a) comprise the phenolic compounds dissolved in dimethylsulfoxide.

3. The method of claim 1, wherein the organic base in step (b) comprises triethylamine.

4. The method of claim 1, wherein the organic base in step (b) comprises diisopropylethylamine.

5. The method of claim 1, wherein the saturated solution of $SO_2F_2$ in step (b) comprises $SO_2F_2$ dissolved in acetonitrile.

6. The method of claim 1, wherein the reactions in step (b) are continued for about 12 hours before step (c).

7. The method of claim 1, wherein each solution of phenolic compound in step (a) comprises about 0.1 µmol of the phenolic compound dissolved in about 10 µL of DMSO.

8. The method of claim 7, wherein the saturated solution of $SO_2F_2$ in step (b) comprises $SO_2F_2$ dissolved in acetonitrile.

9. The method of claim 8, wherein about 100 µL of the saturated solution of $SO_2F_2$ is added to each well in step (b).

10. The method of claim 1 wherein the cancer cell cultures in step (f) comprise A549 adenocarcinomic human alveolar basal epithelial cells.

11. The method of claim 1, wherein the cancer cell cultures in step (f) comprise MCF-7 breast cancer cells.

12. The method of claim 1, wherein the cancer cell cultures in step (f) comprise SKBR3 breast cancer cells.

13. The method of claim 1, wherein the cancer cell cultures in step (f) comprise HT-29 colon cancer cells.

14. The method of claim 1, wherein at least two different concentrations of each candidate arylfluorosulfate anticancer agent are added to the cancer cell cultures in step (f).

15. The method of claim 1, wherein at least five different concentrations of each candidate arylfluorosulfate anticancer agent are added to the cancer cell cultures in step (f).

16. The method of claim 1, wherein the cancer cell cultures in step (f) are incubated at about 37° C. with 5% $CO_2$ for about 24 hours.

17. The method of claim 1, further comprising adding dimethylsulfoxide alone to some of the cell cultures in the second multi-well plate in step (f) as controls.

18. The method of claim 17, wherein the assessing in step (h) comprises calculating a growth inhibition percentage for each candidate arylfluorosulfate anticancer agent by comparing cell growth in the cultures containing the candidate arylfluorosulfate anticancer agent to cell growth of the controls.

19. The method of claim 18, wherein step (f) comprises adding at least five different concentrations of the candidate arylfluorosulfate anticancer agents to the cancer cell cultures; and the assessing in step (h) comprises constructing a dose-response curve from the cancer cell growth at each concentration of each candidate arylfluorosulfate anticancer agent.

20. A high-throughput screening method for identifying anticancer medicinal agents comprising an arylfluorosulfate functional group, the method comprising the sequential steps of:

(a) distributing solutions comprising about 0.1 µmol of phenolic compounds dissolved in dimethylsulfoxide into wells of a first multi-well plate with one phenolic compound per well, wherein each phenolic compound comprises one or more OH substituent on an aromatic moiety and each solution comprises about 1 µmol of the phenolic compound;

(b) adding to each well of said first multi-well plate about 10 equivalents of an organic base and about 100 µL of a saturated solution of $SO_2F_2$, thereafter sealing each well, thereby initiating reactions between said OH substituents of the phenolic compounds with the $SO_2F_2$ and forming candidate arylfluorosulfate anticancer agents therefrom;

(c) adding an excess of trimethylsilanol to each well in the first multi-well plate after the reaction in step (b) is complete to convert fluoride ion formed from the reaction of the phenolic compound and the $SO_2F_2$ into trimethylsilyl fluoride;

(d) evaporating, in vacuo, dimethylsulfoxide, the organic base, and trimethylsilyl compounds present in the wells to leave a residue of a candidate arylfluorosulfate anticancer agent in each well;

(e) dissolving each residue in about 10 µL of dimethylsulfoxide to form solutions of the candidate arylfluorosulfate anticancer agents;

(f) adding at least two concentrations of the candidate arylfluorosulfate anticancer agent solutions from step (e) in the range of about $2\times10^{-7}$ µM to about 20 µM to cancer cell cultures distributed in wells of a second multi-well plate at cell concentrations of about 3000 to about 5000 cells per well;

(g) incubating the cell cultures in the second multi-well plate under conditions suitable for viability or growth of the cancer cells; and (h) assessing the effect of the candidate arylfluorosulfate anticancer medicinal agents on the viability or growth of the cancer cells.

* * * * *